US005686544A

United States Patent [19]

Pocius

[11] Patent Number: 5,686,544
[45] Date of Patent: Nov. 11, 1997

[54] ORGANOBORANE POLYAMINE COMPLEX INITIATOR SYSTEMS AND POLYMERIZABLE COMPOSITIONS MADE THEREWITH

[75] Inventor: Alphonsus V. Pocius, Maplewood, Minn.

[73] Assignee: Minnesota Mining and Manufacturing Company, St. Paul, Minn.

[21] Appl. No.: 514,190

[22] Filed: Aug. 11, 1995

[51] Int. Cl.$^6$ .............................. C08F 4/52; C08L 75/04
[52] U.S. Cl. ................... 526/196; 526/197; 526/198; 526/208; 525/130; 525/131; 525/134; 525/459
[58] Field of Search .................................. 376/196, 197, 376/198, 208; 525/130, 131, 134, 459

[56] References Cited

U.S. PATENT DOCUMENTS

| | | | |
|---|---|---|---|
| 2,985,633 | 5/1961 | Welch et al. | 526/147 |
| 3,141,862 | 7/1964 | Kirshenbaum et al. | 525/251 |
| 3,275,611 | 9/1966 | Mottus et al. | 526/186 |
| 3,340,193 | 9/1967 | Fields et al. | 252/56 |
| 3,418,260 | 12/1968 | Trofimenko | 528/4 |
| 3,425,988 | 2/1969 | German et al. | 528/50 |
| 3,451,952 | 6/1969 | Slocombe | 528/75 |
| 3,476,727 | 11/1969 | Lo Monaco et al. | 526/65 |
| 3,527,737 | 9/1970 | Masuhara et al. | 525/251 |
| 3,829,973 | 8/1974 | Masuhara et al. | 32/15 |
| 4,043,982 | 8/1977 | O'Sullivan et al. | 526/248 |
| 4,167,616 | 9/1979 | Bollinger | 526/197 |
| 4,515,724 | 5/1985 | Ritter | 526/197 |
| 4,638,092 | 1/1987 | Ritter | 568/1 |
| 4,639,498 | 1/1987 | Ritter | 526/196 |
| 4,656,229 | 4/1987 | Chiao | 525/518 |
| 4,676,858 | 6/1987 | Ritter | 156/307.3 |
| 4,684,538 | 8/1987 | Klemarczyk | 427/54.1 |
| 4,721,751 | 1/1988 | Schappert et al. | 524/773 |
| 4,731,416 | 3/1988 | Saunders | 525/131 |
| 4,920,188 | 4/1990 | Sakashita et al. | 526/196 |
| 4,921,921 | 5/1990 | Ritter | 526/195 |
| 4,985,516 | 1/1991 | Sakashita et al. | 526/196 |
| 5,021,507 | 6/1991 | Stanley et al. | 525/127 |
| 5,106,928 | 4/1992 | Skoultchi et al. | 526/196 |
| 5,143,884 | 9/1992 | Skoultchi et al. | 502/160 |
| 5,286,821 | 2/1994 | Skoultchi | 526/196 |
| 5,310,835 | 5/1994 | Skoultchi et al. | 526/198 |
| 5,376,746 | 12/1994 | Skoultchi | 526/196 |
| 5,401,805 | 3/1995 | Chung et al. | 525/288 |

FOREIGN PATENT DOCUMENTS

| | | | |
|---|---|---|---|
| 2061021 | 10/1992 | Canada | C09D 157/00 |
| 46-16888 | 5/1971 | Japan . | |
| 48-18928 | 6/1973 | Japan | C09J 5/00 |
| 53-102394 | 9/1978 | Japan | C08F 4/40 |
| 62-288675 | 12/1987 | Japan | C09J 3/14 |
| 3-177470 | 8/1991 | Japan . | |
| 3-264509 | 11/1991 | Japan | A61K 6/00 |
| 93-235089 | 9/1993 | Japan | A61K 6/00 |
| 1113722 | 5/1968 | United Kingdom . | |
| 1132261 | 10/1968 | United Kingdom . | |

OTHER PUBLICATIONS

The Trialkylborane-initiated Graft Copolymerization of Methyl Methacrylate onto Hemoglobin, K. Kojima, S. Iwabuchi and K. Kojima, *Bulletin of the Chemical Society of Japan*, vol. 44, pp. 1891–1895 (1971).
A New Method for the Graft Copolymerization of Methyl Methacrylate onto Proteins and Fibers, *Polymer Letters*, vol. 9, pp. 25–29 (1971).
The Grafting of Methyl Methacrylate onto Cotton by Tri–n–butylborane, K. Kojima, S. Iwabuchi, K. Murakami, K. Kojima and F. Ichikawa, *Journal of Applied Polymer Science*, vol. 16, pp. 1139–1148 (1972).
Grafting of Vinyl Monomers by Tri–n–Butylborane onto Chlorophyll and Related Compounds, *Polymer Letters Edition*, vol. 13, pp. 361–363 (1975).
Tributylborane–Initiated Grafting of Methyl Methacrylate onto Chitin, K. Kojima, M. Yoshikuni and T. Suzuki, *Journal of Applied Polymer Science*, vol. 24, pp. 1587–1593 (1979).
Grafting of Methyl Methacrylate onto Silk Fibers Initiated by Tri–n–Butylborane, M. Tsukada, T. Yamamoto, N. Nakabayashi, H. Ishikawa and G. Freddi, *Journal of Applied Polymer Science*, vol. 43, pp. 2115–2121 (1991).
Molecular Weight Distribution of the Methyl Methacrylate (MMA) Polymer Separated from the MMA-Grafted Silk Fiber, M. Tsukada, Y. Goto, G. Freddi, T. Yamamoto and N. Nakabayashi, *Journal of Applied Polymer Science*, vol. 44, pp. 2197–2202 (1992).
Synthesis of Functionalized Polypropylene and Polypropylene-Polymethylmethacrylate Graft Copolymer, D. Rhubright and T.C. Chung, Proceedings of the American Chemical Society, *Polymeric Materials Science and Engineering*, vol. 67, pp. 112–113 (1992).
Polymerization of Acrylonitrile in Presence of Tributylborine, G. Kolesnikov and L. Fedorova, translated from *Bull. Acad. Sci. USSR, Div. Chem. Sci.*, p. 236 (1957).
Tributylborine: A Catalyst for the Polymerization of unsaturated Compounds, G. Kolesnikov and N.V. Klimentova, translated from *Bull. Acad. Sci. USSR, Div. Chem. Sci.*, p. 653 (1957).
Triethylboron as an Initiator for Vinyl Polymerization, J. Furukawa, T. Tsuruta and S. Inoue, *Journal of Polymer Science*, vol. XXVI, Issue No. 113, pp. 234–236 (1957).

(List continued on next page.)

Primary Examiner—James J. Seidleck
Assistant Examiner—P. Hampton-Hightower
Attorney, Agent, or Firm—Gary L. Griswold; Walter N. Kirn; Steven E. Skolnick

[57] ABSTRACT

A composition comprises organoborane polyamine complex and polyol. The composition can form a part of a polymerization initiator system that also includes polyisocyanate. The system can be used to initiate polymerization of acrylic monomer and to form a polyurethane/polyurea acrylic adhesive that has exceptionally good adhesion to low surface energy polymers.

42 Claims, No Drawings

OTHER PUBLICATIONS

Oxygen Compounds as Cocatalyst for Triethylboron–Catalyzed Vinyl Polymerization, J. Furukawa and T. Tsuruta, *Journal of Polymer Science*, vol. XXVIII, Issue No. 116, pp. 227–229 (1958).

Mechanism of the Polymerization of Acrylonitrile in Presence of Tributylborine, G. Kolesnikov and L. Fedorova, translated from *Bull. Acad. Sci. USSR, Div. Chem. Sci.*, p. 906 (1958).

Mechanism of Trialkylboron Initiated Polymerization, J. Fordham and C. Sturm, *Journal of Polymer Science*, vol. XXXIII, No. 126, pp. 503–504 (1958).

Cocatalytic Activity of Some Metal Salts on Vinyl Polmerization with Tributhylboron, I.M. Panayotov, *Comptes rendus de l'Academie bulgare des Sciences*, vol. 14, No. 2, pp. 147–150 (1961).

Polymerization with Organoboron Compounds, F. Arimoto, *Journal of Polymer Science: Part A–1*, vol. 4, pp. 275–282 (1966).

On the Existence of a Free–Radical Organoboron Complex in the Polymerization of Methyl Methacrylate, R. Kern and J. Schaefer, *Polymer Letters*, vol. 5, pp. 157–162 (1967).

Vinyl Monomer Polymerization Mechanism in the Presence of Trialkylboranes, J. Grotewold, E. Lissi and A. Villa, *Journal of Polymer Science: Part A–1*, vol. 6, pp. 3157–3162 (1968).

Free–Radical Polymerization of Methyl Methacrylate in the Presence of Trialkylboranes, P. Brindley and R. Pearson, *Polymer Letters*, vol. 6, pp. 831–835 (1968).

Ethylene Polymerization in Presence of Tributylboron, G. Kolesnikov and T. Soboleva, *Scientific and Research Publications of the Members of the All Union Chemical Society Name After Mendilev*, vol. 2, p. 663 (1957).

Studies on Dental Self–Curing Resins (II), S. Fujisawa, Y. Imai and E. Masuhara, *Reports of the Institute for Medical & Dental Engineering*, vol. 3, pp. 64–71 (1969).

Free–Radical Copolymerization of 1,2–Dichloroethylenes. Evidence for Chain Transfer by Chlorine Atom Elimination, T. Dawson, R. Lundberg and F. Welch, *Journal of Polymer Science: Part A–1*, vol. 7, pp. 173–181 (1969).

Mechanism of Vinyl Monomer Polymerization in the Presence of Trialkylboranes and Inhibitors, E. Aranchibia et al., *Journal of Polymer Science: Part A–1*, vol. 7, pp. 3430–3433 (1969).

Polymerization of Methyl Methacrylate by Trialkylborane–Pyridine System, K. Kojima et al., *Polymer Letters*, vol. 8, pp. 541–547 (1970).

Polymerization Initiated by Triethylborane–Peroxide Mixtures, E. Abuin et al., *Polymer Letters*, vol. 7, pp. 515–518 (1970).

Polymerization of Methyl Methacrylate by Co–ordination Compounds of Tri–n–butylborane with Some Electron–donating Compounds, Kojima et al., *Research Report of the Chiba University Faculty of Engineering*, vol. 22, No. 41, pp. 47–55.

Polymerization of Methyl Methacrylate Initiated by Tri–n–butylborane–Organic Halide Systems, M. Yoshikuni, M. Asami, S. Iwabuchi and K. Kojima, *Journal of Polymer Science*, vol. 11, pp. 3115–3124 (1973).

Polymerization of Methyl Methacrylate Initiated by Tributylborane–Pyridine System, Kojima et al., *Journal of the Japanese Chemical Society*, No. 11, pp. 2165–2171 (1972).

The Copolymerization of Vinylhydroquinone and Acrylonitrile by Tri–n–butylborane, S. Iwabuchi, M. Ueda, M. Kobayashi and K. Kojima, *Polymer Journal*, vol. 6, No. 2, pp. 185–190 (1974).

Free Radical Polymerization in the Presence of Triethylborane, E. Abuin, J. Cornejo and E. Lissi, *European Polymer Journal*, vol. 11, pp. 779–782 (1975).

Polymerization of Methyl Methacrylate by tri–n–butylborane in the presence of amino acid esters, K. Kojima, S. Iwabuchi, Y. Moriya and M. Yoshikuni, *Polymer*, vol. 16, pp. 601–604 (1975).

Analysis of Mechanism of Radical Formation Resulted from the Initiator System of Triethylboron and Oxygen by Spin Trapping Technique, Sato et al., *Journal of the Japanese Chemical Society*, No. 6, pp. 1080–1084 (1975).

Development of Adhesive Pit and Fissure Sealants Using a MMA Resin Initiated by a Tri–n–butyl Borane Derivative, N. Nakabayashi and E. Masuhara, *Journal of Biomedical Materials Research*, vol. 12, pp. 149–165 (1978).

Vinyl Acetate Polymerization Initiated by Alkylborane–oxidizer–type Systems, S. Ivanchev, L. Shumnyi and V. Konovalenko, *Polymer Science U.S.S.R.*, vol. 22, No. 12, pp. 8000–8006 (1980).

Preparation of Hard Tissue Compatible Materials: Dental Polymers, N. Nakabayashi and E. Masuhara, *Biomedical Polymers*, pp. 85–111 (1980).

Mechanism of Initiation of Polymerization of Vinyl Monomers by Means of the Trialkylborane–Acid System, S. Ivanchev and L. Shumnyi, translated from *Doklady Akademii Nauk SSSR*, vol. 270, No. 5, pp. 1127–1129 (1983).

Effect of Organic Bases on Initiating Properties in the System Boronalkylelemental Organic Peroixde During Vinylchloride Polymerization, T. Guzanova, Master Thesis of the Fifth (graduate) year student, Ministry of High and Secondary Special Education Russia, Gorky State University (1983).

Application of Spin Trapping Technique to Radical Polymerization, 20, T. Sato, N. Fukumura and T. Otsu, *Makromol. Chem.*, 184, pp. 431–442 (1983).

Importance of Polymerization Initiator Systems and Interfacial Initiation of Polymerization in Adhesive Bonding of Resin to Dentin, Y. Imai, Y. Kodoma, K. Kojima, T. Akimoto, K. Ikakura and T. Ohta, *J. Dent. Res.*, vol. 70, No. 7, pp. 1088–1091 (1991).

Vibrational Analysis by Raman Spectroscopy of the Interface Between Dental Adhesive Resin and Dentin, M. Suzuki, H. Kato and S. Wakumoto, *J. Dent. Res.*, vol. 70, No. 7, pp. 1092–1097 (1991).

Laser–Raman Spectroscopic Study of the Adhesive Interface Between 4–MET/MMA–TBB Resin and Hydroxyapatite or Bovine Enamel, M. Ozaki, M. Suzuki, K. Itoh and S. Wakamoto, *Dental Materials Journal*, vol. 10, No. 2, pp. 105–120 (1991).

Polymerization of Some Vinyl Monomers on Triisobutylboron–Containing Radical Initiators in the Presence of Hydroquinone and Benzoquinone, V. Dodonov and D. Grishin, *High Molecular Compounds*, vol. 35, No. 3, pp. 137–141 (1993).

Synthesis of PP–g–PMMA, PP–g–PVA and PP–g–PCL Copolymers, D. Rhubright and T. Chung, American Chemical Society, Division of Polymer Chemistry, Papers Presented at the Chicago, Illinois Meeting, vol. 34, No. 2, pp. 560–561 (1993).

Functionalized and Grafted Polyolefin Copolymers Prepared by Tansition Metal Catalysts and Borane Monomers, T. Chung, *Polymer Reprints*, vol. 35, No. 1, pp. 674–675 (1994).

Photochemical Modification of Fluorocargon Resin Surface to Adhere with Epoxy Resin, M. Okoshi, T. Miyokawa, H. Kashiura and M. Murahara, *Mat. Res. Soc. Symp. Proc.*, vol. 334, pp. 365–371 (1994).

Chemical Abstract No. 88532r, *Chemical Abstracts*, vol. 73, 1970.

Chemical Abstract No. 134385q, *Chemical Abstracts*, vol. 80, 1974.

ORGANOBORANE POLYAMINE COMPLEX INITIATOR SYSTEMS AND POLYMERIZABLE COMPOSITIONS MADE THEREWITH

BACKGROUND OF THE INVENTION

1. Field of the Invention

This invention relates generally to organoborane polyamine complex initiator systems and, more specifically, to systems in which the complex is carried in a polyol, and to systems that include polyisocyanate. The invention further relates to polymerizable compositions made therewith, particularly two-part adhesive compositions that have independent polyurethane/polyurea and acrylic components when cured. The adhesive compositions have excellent adhesion to a variety of substrates, especially low surface energy polymers.

2. Description of the Related Art

An efficient, effective means for adhesively bonding low surface energy plastic substrates such as polyethylene, polypropylene and polytetrafluoroethylene (e.g., TEFLON) has long been sought. The difficulties in adhesively bonding these materials are well known. See, for example, "Adhesion Problems at Polymer Surfaces" by D. M. Brewis that appeared in *Progress in Rubber and Plastic Technology*, volume 1, page 1 (1985). The conventional approaches typically function by: (1) increasing the surface energy of the substrate (to more closely match the surface energies of the substrate and the adhesive thereby promoting better wetting of the substrate by the adhesive) and/or (2) eliminating additives and low molecular weight polymer fractions in the substrate that can migrate to the substrate surface and adversely affect adhesion by forming a weak boundary layer.

As a result, the conventional approaches often use complex and costly substrate surface preparation techniques such as flame treatment, corona discharge, plasma treatment, oxidation by ozone or oxidizing acids, and sputter etching. Alternatively, the substrate surface may be primed by coating it with a high surface energy material. However, to achieve adequate adhesion of the primer, it may be necessary to first use the surface preparation techniques described above. All of these techniques are well known, as reported in *Treatise on Adhesion and Adhesives* (J. D. Minford, editor, Marcel Dekker, 1991, New York, volume 7, pages 333 to 435). The known approaches are frequently customized for use with specific substrates. As a result, they may not be useful for bonding low surface energy plastic substrates generally.

Moreover, the complexity and cost of the presently known approaches do not render them particularly suitable for use by the retail consumer (e.g., home repairs, do-it-yourselfers, etc.) or in low volume operations. One vexing problem is the repair of many inexpensive everyday household articles that are made of polyethylene, polypropylene or polystyrene such as trash baskets, laundry baskets and toys.

Consequently, there has been a considerable and long felt need for a simple, easy to use adhesive that can readily bond a wide variety of substrates, especially low surface energy materials, such as polyethylene, polypropylene and polytetrafluoroethylene, without requiring complicated surface preparation, priming and the like.

While an adhesive that can bond low surface energy plastics is certainly advantageous, the commercial utility of such an adhesive would be enhanced if the components thereof could be combined in a convenient mix ratio. This would permit facile application of the adhesive using conventional adhesive dispensers without the need for laborious hand weighing and mixing of the different components. However, the convenient mix ratio should not come at the expense of significantly reduced storage stability or performance. Thus, there is not only a need for an adhesive that can bond low surface energy plastics, but a need for such an adhesive that can be readily blended in a convenient mix ratio without a material reduction in storage stability or performance.

It may be desirable for such adhesives to possess other attributes. For example, in certain applications it may be important for the adhesive to be tough, elastomeric or abrasion resistant, properties typically associated with polyurethane adhesives. In addition, it may be important to eliminate or reduce low molecular weight components in the adhesive that could migrate to the interface between the adhesive and the substrate. This could adversely affect adhesion by forming a weak boundary layer. Furthermore, if the low molecular weight components are solvent extractable, adhesive volume could be lost, voids could be created in the adhesive, and the adhesive and cohesive strength of the bond could be weakened if the bonded article was exposed to solvent. Also, low molecular weight components may be sensitive to water and their migration to the adhesive/substrate interface could decrease the hydrolytic stability of the adhesive bond.

As explained more fully hereinbelow, the organoborane polyamine complex initiator systems and the related compositions of the invention (which may include polyisocyanate, polyol, and acrylic monomer that can polymerize to polyurethane/polyurea acrylic adhesives) not only satisfy these demands but offer many other advantages.

Organoboranes such as tributylborane and triethylborane have been reported to initiate and catalyze the polymerization of vinyl monomers (see, for example, G. S. Kolesnikov et al., Bull. Acad. Sci. USSR, Div. Chem. Sci. 1957, p. 653; J. Furakawa et al., Journal of Polymer Science, volume 26, issue 113, p. 234, 1957; and J. Furakawa et al., Journal of Polymer Science, volume 28, issue 116, 1958). The organoborane compounds of the type described in these references are known to be quite pyrophoric in air which complicates facile use.

Chemical Abstracts No. 134385q (volume 80, 1974) "Bonding Polyolefin or Vinyl Polymers" reports that a mixture of 10 parts methyl methacrylate, 0.2 part tributylborane, and 10 parts poly(methylmethacrylate) was used to bond polyethylene, polypropylene and poly(vinyl acetate) rods.

U.S. Pat. No. 3,275,611 to E. H. Mottus et al. discloses a process for polymerizing olefinic compounds (e.g., methacrylate monomers) with a catalyst comprising an organoboron compound, a peroxygen compound, and an amine. The organoboron compound and the amine may be added to the reaction mixture separately or they may be added as a performed complex.

British Patent Specification No. 1,113,722 "Aerobically Polymerisable Compositions," published May 15, 1968 discloses the polymerization of acrylate monomers through the use of a free-radical catalyst (e.g., peroxides) and triarylborane complexes having the general formula $(R)_3B$-Am wherein R is an aryl radical and Am is an amine. The resulting compositions are reportedly useful as adhesives.

Chemical Abstracts No. 88532r (volume 73, 1970) "Dental Self-curing Resin" and the full text paper to which it refers report that tributylborane can be made stable in air by complexing it with ammonia or certain amines and that the tributylborane can be reactivated with an amine acceptor such as an isocyanate, an acid chloride, a sulfonyl chloride, or anhydrous acetic acid. As a result, the complex can be used to polymerize blends of methyl methacrylate and poly(methylmethacrylate) to provide a dental adhesive.

A series of patents issued to Skoultchi or Skoultchi et al. (U.S. Pat. Nos.: 5,106,928; 5,143,884; 5,286,821; 5,310,835; and 5,376,746) disclose a two part initiator system that is reportedly useful in acrylic adhesive compositions, especially elastomeric acrylic adhesives. The first part of the two part system includes a stable organoborane amine complex and the second part includes a destabilizer or activator such as an organic acid or an aldehyde.

The adhesive compositions are reportedly particularly useful in structural and semi-structural applications such as speaker magnets, metal-metal bonding, (automotive) glass-metal bonding, glass-glass bonding, circuit board component bonding, selected plastic to metal, glass, wood, etc. bonding, and electric motor magnets. Those plastics that may be bonded are not further described.

U.S. Pat. No. 4,043,982 (O'Sullivan et al.) describes a composition useful as an adhesive and which includes an acyl or silyl peroxide-type polymerization initiator (generally dissolved in a volatile solvent), a polymerizable acrylate-isocyanate monomer or oligomer, and an aryl amine polymerization initiator. The polymerizable acrylate-isocyanate monomer is the reaction product of an organic polyisocyanate with a polymerizable acrylate ester having a hydroxy or a primary or secondary amino group in the alcoholic moiety.

U.S. Pat. No. 4,721,751 (Schappert et al.) describes polyurea-polyurethane acrylate dispersions which are reportedly useful as adhesives and sealants. The materials can be prepared by reacting a polyisocyanate with a polyfunctional amine in the presence of a polyol, an ethylenically unsaturated diluent free of active hydrogens, and an active hydrogen containing polymerizable ethylenically unsaturated compound.

U.S. Pat. No. 4,731,416 (Saunders) describes a polyurethane-type adhesive comprising the reaction product of: (1) a true solution of a (a) copolymer of an α,β-ethylenically unsaturated carboxylic acid and a hydroxyalkyl ester of an α,β-ethylenically unsaturated acid in (b) a polyahl having a molecular weight of at least 200; (2) an organic polyisocyanate; and (3) a polyahl chain extender having a molecular weight of less than 200.

U.S. Pat. No. 5,021,507 (Stanley et al.) describes an acrylic modified reactive urethane hot melt adhesive which can be obtained by adding a urethane prepolymer to low molecular weight polymers formed from ethylenically unsaturated monomers which do not contain active hydrogen.

SUMMARY OF THE INVENTION

In general, this invention pertains to polymerization initiator systems that are particularly useful in providing two-part curable compositions, especially those that cure (i.e., polymerize) to polyurethane/polyurea acrylic adhesives. Broadly, and in one aspect of the invention, the polymerization initiator systems include organoborane polyamine complex and polyol. Preferably, the complex and the polyol form a solution (even more preferably a liquid solution) at room temperature.

A variety of organoborane polyamine complexes may be used in the invention. The following structure is representative of those that are suitable:

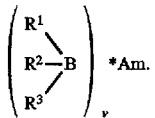

In this structure:
R$^1$ is an alkyl group having 1 to 10 carbon atoms;
R$^2$ and R$^3$ are independently selected from alkyl groups having 1 to 10 carbon atoms and phenyl-containing groups;
Am is a polyamine selected from the group consisting of alkyl polyamine, polyoxyalkylenepolyamine, and the reaction product of a diprimary amine-terminated material and a material having at least two groups reactive with primary amine, wherein the number of primary amine groups in the reaction mixture was greater than the number of groups reactive with primary amine; and
the value of v is selected so as to provide an effective ratio of primary amine nitrogen atoms to boron atoms in the complex, which, broadly, is a ratio of about 0.5:1 to 4:1, although a 1:1 ratio is more preferred.

A wide variety of polyols may be used, including polyether polyols and polyester polyols. Preferably, the polyol has a hydroxyl functionality of 2 to 3. Among those polyols which are particularly preferred are polyalkylene oxide polyols such as polyethylene oxide polyol, polypropylene oxide polyol, polytetramethylene oxide polyol, ethylene oxide- and propylene oxide-terminated derivatives of these materials, and blends. Poly-ε-caprolactone polyol is a particularly preferred polyester polyol.

The polymerization initiator systems of the invention further include a polyisocyanate (preferably a diisocyanate). The polyisocyanate is reactive with the polyamine of the complex and can liberate the organoborane for initiating polymerization of acrylic monomer. Preferably, the number of equivalents of isocyanate functionality is equal to the sum of the number of equivalents of amine functionality plus the number of equivalents of hydroxyl functionality in the composition. As a result, and quite advantageously, condensation polymerization of the remaining polyisocyanate occurs by reaction with the polyol so as to form independent but coexisting linear polymers or networks of acrylic and polyurethane/polyurea.

The amount of low molecular weight, migratory polyisocyanate-polyamine reaction product in the composition is reduced by forming a linear polymer or network of polyurethane/polyurea. Otherwise, such migratory components could bloom to the interface between the adhesive composition and a substrate, which could result in a weak boundary layer, decreased hydrolytic stability, reduced adhesion and a loss of cohesive strength, especially if these components are solvent extractable. In certain applications this could be undesirable.

In another aspect, the invention relates to a polymerizable composition comprising organoborane polyamine complex, polyol, polyisocyanate, and polymerizable acrylic monomer. The polymerizable acrylic monomer is preferably a monofunctional acrylate ester or a monofunctional methacrylate ester (including substituted derivatives and blends of these materials). A blend of an alkyl acrylate and an alkyl methacrylate is particularly preferred.

Optionally, the polymerizable composition may include a bireactive compound; i.e., a compound containing both a free-radically polymerizable group (preferably (meth) acrylic functionality) and an amine reactive group. The bireactive compound can be directly included in the adhesive composition or it can be generated in situ; for example, by reacting a hydroxylated (meth)acrylate with the polyisocyanate.

The polymerizable compositions are particularly useful in providing a 100% solids, two-part, curable (at room temperature) adhesive composition. One part comprises organoborane polyamine complex and polyol (preferably as a solution). The other part comprises polymerizable acrylic monomer, polyisocyanate, and optionally, bireactive compound. The polyisocyanate is provided in an amount sufficient to liberate the organoborane for initiating polymerization of the acrylic monomer, and for reacting with the polyamine and the polyol to form polyurethane/polyurea. The two parts of the adhesive may be readily combined in a convenient, commercially useful, whole number mix ratio of 1:10 or less, more preferably 1:4, 1:3, 1:2 or 1:1, such that they can be easily used with two-part adhesive dispensers. When cured, these compositions yield a linear polymer or network of acrylic, a linear polymer or network of polyurethane/polyurea that is independent from but coexists with the polymerized acrylic, and residual organoborane and/or organoborane degradation (e.g., by oxidation) by-products. If a bireactive compound has been included, it can link the polymerized acrylic and polyurethane/polyurea.

The compositions of the invention have excellent adhesion to low surface energy substrates such as polyethylene, polypropylene and polytetrafluoroethylene. Thus, in another aspect, the invention relates to bonded composites comprising a first substrate and a second substrate (preferably low surface energy polymeric materials) adhesively bonded together by a layer of a cured adhesive composition according to the invention. Adhesion to such substrates is promoted by using an effective amount of the organoborane polyamine complex, which is broadly about 0.03 to 1.5 weight % boron, based on the weight of acrylic-group containing components and organic thickener in the polymerizable composition, more preferably about 0.08 to 0.5 weight % boron, most preferably 0.1 to 0.3 weight % boron.

The solubility of the organoborane polyamine complex in polyol enables the provision of two-part adhesives as described above. The complex can be separated from constituents with which it may react. This can improve the storage stability of the adhesive composition. Consequently, the invention also relates to a method of improving the storage stability of a two-part polymerizable adhesive composition that comprises polymerizable acrylic monomer, organoborane polyamine complex, and a material that reacts with the polyamine for liberating the organoborane to initiate polymerization of the acrylic monomer (e.g., the polyisocyanate). The method comprises the steps of:

(a) providing the organoborane polyamine complex;
(b) providing a polyol in which the organoborane polyamine complex is soluble;
(c) forming a solution of the polyol and the organoborane polyamine complex; and
(d) preparing a two-part polymerizable adhesive composition in which one part comprises the material that reacts with the polyamine and all of the polymerizable acrylic monomer, and the other part comprises the solution of the polyol and the organoborane polyamine complex.

As noted above, the amount of migratory polyisocyanate-polyamine reaction product is reduced by forming polyurethane/polyurea. Consequently, the invention also relates to a method for reducing the amount of migratory material in adhesive compositions of the type described above. The method comprises the steps of:

(a) providing a polyisocyanate that is reactive with the polyamine component of the complex;
(b) providing a polyol that is reactive with the polyisocyanate;
(c) permitting the polyisocyanate to react with the polyamine to liberate the organoborane;
(d) initiating polymerization of the acrylic monomer with the liberated organoborane and polymerizing the acrylic monomer to form a linear polymer or network of acrylic; and
(e) permitting the polyamine, polyisocyanate and polyol to react to form a linear polymer or network of polyurethane/polyurea that is independent from but coexists with the linear polymer or network of acrylic.

DETAILED DESCRIPTION OF THE PREFERRED EMBODIMENTS

In general, this invention pertains to polymerization initiator systems that are particularly useful in providing two-part curable compositions, especially those that cure (i.e., polymerize) to polyurethane/polyurea acrylic adhesives. Broadly, and in one aspect of the invention, the polymerization initiator systems include organoborane polyamine complex and polyol. As explained below, the polyol is advantageously both a carrier for the organoborane polyamine complex and reactive with other constituents of the polymerization initiator system. More specifically, the polymerization initiator systems of the invention comprise and, more preferably, consist essentially of organoborane polyamine complex, polyol, and polyisocyanate.

The organoborane component of the complex initiates free-radical polymerization of acrylic monomer to form an acrylic component. To stabilize the organoborane against premature oxidation, it is complexed with polyamine. The organoborane is liberated from the complex by reacting a portion of the polyisocyanate with the polyamine so as to form polyurea. Quite advantageously, condensation polymerization of the remaining polyisocyanate occurs by reaction with the polyol so as to form a polyurethane/polyurea component that is independent from but coexists with the acrylic. That is, an independent linear polymer or network of polyurethane/polyurea forms, and an independent linear polymer or network of acrylic forms (which coexist with each other), as opposed to generating a hybrid "urethane-acrylate" material (i.e., a material having a urethane backbone with acrylic functionality either on the backbone or terminally, or a material having an acrylic backbone with urethane or isocyanate functionality either on the backbone or terminally).

Advantageously, incorporating the polyamine into the polymerized composition reduces the level of low molecular weight components that could bloom or migrate to the adhesive/substrate interface. In the case of an adhesive, this could cause a weak boundary layer, reduced adhesion, and an increased level of extractable components. As explained below, the independent polyurethane/polyurea and acrylic components may be linked together by a bireactive compound (i.e., a monomer having both amine-reactive and free-radically polymerizable functionalities) to provide more rapid strength build-up and even further reduce the level of low molecular weight migratory components.

The polyurethane/polyurea acrylic adhesives of the invention can bond a wide variety of substrates, but provide exceptionally good adhesion to low surface energy plastic substrates (e.g., polyethylene, polypropylene, polytetrafluoroethylene, etc.) that, heretofore, have been bonded using complex and costly surface preparation techniques.

The polymerized polyurethane/polyurea acrylic compositions derive their adhesion, especially to low surface energy plastics, from the organoborane-initiated free-radical polymerization of the acrylic monomer. The compositions derive their cohesive strength from the simultaneous organoborane-initiated polymerization of acrylic monomer, and the condensation polymerization of polyisocyanate with the polyol carrier for the complex and the polyamine from the complex. Most advantageously, the compositions of the invention offer both good adhesion from the polymerized acrylic, and a tough, elastomeric, abrasion resistant bond from the polyurethane/polyurea.

The polyol, polyisocyanate and acrylic monomer are, individually, reactive materials with molecular weights (or weight average molecular weights) of less than about 3,000, more preferably less than about 1,000, and most preferably less than about 750. As a result, the invention also provides a fully reactive, 100% solids, polymerizable adhesive composition. Moreover, the polyol carrier enables the provision of a storage stable initiator system that can be directly combined with polymerizable monomers for a two-part adhesive in a convenient, commercially useful, whole number mix ratio of 1:10 or less.

Organoborane polyamine complexes useful in the invention are complexes of organoborane and polyamine. They preferably have the following general structure:

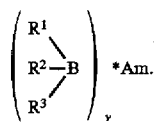

where $R^1$ is an alkyl group having 1 to 10 carbon atoms, and $R^2$ and $R^3$ are independently selected from alkyl groups having 1 to 10 carbon atoms and phenyl-containing groups. More preferably, $R^1$, $R^2$ and $R^3$ are alkyl groups having 1 to 5 carbon atoms such as methyl, ethyl, propyl, iso-propyl, n-butyl, iso-butyl, and pentyl. By "independently selected" it is meant that $R^2$ and $R^3$ may be the same or that they may be different. $R^1$ may be the same as $R^2$ or $R^3$, or it may be different. Preferably $R^1$, $R^2$ and $R^3$ are the same. Most preferred are complexes in which $R^1$, $R^2$ and $R^3$ are each ethyl groups.

The value of v is selected so as to provide an effective ratio of primary amine nitrogen atoms to boron atoms in the complex. The primary amine nitrogen atom to boron atom ratio in the complex is broadly about 1:1 to 4:1. Preferably, however, the ratio is about 1:1 to 2:1, more preferably about 1:1 to 1.5:1, and most preferably about 1:1. (In the case of a polyamine that contains both primary and secondary amine groups, the ratio of primary amine nitrogen atom to boron atom could be as low as 0.5:1 .) A primary amine nitrogen atom to boron atom ratio of less than 1:1 could leave free organoborane, a material that tends to be pyrophoric. At primary amine nitrogen atom to boron atom ratios in excess of 2:1, the practical utility of the complex in, for example, an adhesive system diminishes as the amount of complex that must be employed to generate a useful adhesive becomes larger.

"Am" represents the polyamine portion of the complex and may be provided by a wide variety of materials having more than one amine group, including blends of different polyamines. More preferably, the polyamine has two to four amine groups, although polyamines with two amine groups (i.e., diamines) are most preferred.

In one embodiment, the polyamine may be described by the structure $H_2N-R^4-NH_2$ in which $R^4$ is a divalent, organic radical comprised of an alkyl, aryl or alkylaryl group. Preferred among these materials are alkane diamines which may be branched or linear, and having the general structure

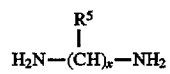

in which x is a whole number greater than or equal to 1, more preferably about 2 to 12, and $R^5$ is hydrogen or an alkyl group, preferably methyl. Particularly preferred examples of alkane diamines include 1,2-ethanediamine, 1,3-propanediamine, 1,5-pentanediamine, 1,6-hexanediamine, 1,12-dodecanediamine, 2-methyl-1,5-pentane diamine, 3-methyl-1,5-pentane diamine, and isomers of these materials. While alkane diamines are preferred, other alkyl polyamines may be used such as triethylene tetraamine and diethylene triamine.

The polyamine may also be provided by a polyoxyalkylenepolyamine. Polyoxyalkylenepolyamine useful in making complexes for the invention may be selected from the following structures:

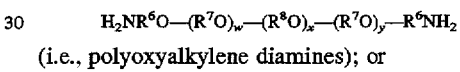

(i.e., polyoxyalkylene diamines); or

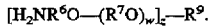

$R^6$, $R^7$ and $R^8$ are alkylene groups having 1 to 10 carbon atoms and may be the same or may be different. Preferably, $R^6$ is an alkyl group having 2 to 4 carbon atoms such as ethyl, n-propyl, iso-propyl, n-butyl or iso-butyl. Preferably, $R^7$ and $R^8$ are alkyl groups having 2 or 3 carbon atoms such as ethyl, n-propyl or iso-propyl. $R^9$ is the residue of a polyol used to prepare the polyoxyalkylenepolyamine (i.e., the organic structure that remains if the hydroxyl groups are removed). $R^9$ may be branched or linear, and substituted or unsubstituted (although substituents should not interfere with oxyalkylation reactions).

The value of w is $\geq 1$, more preferably about 1 to 150, and most preferably about 1 to 20. Structures in which w is 2, 3 or 4 are useful too. The value of x and y are both $\geq 0$. The value of z is >2, more preferably 3 or 4 (so as to provide, respectively, polyoxyalkylene triamines and tetraamines). It is preferred that the values of w, x, y and z be chosen such that the resulting complex is a liquid at room temperature as this simplifies handling and mixing thereof. Usually, the polyoxyalkylenepolyamine is itself a liquid. For the polyoxyalkylene, molecular weights of less than about 5,000 may be used, although molecular weights of about 1,000 or less are more preferred, and molecular weights of about 250 to 1,000 are most preferred.

Examples of particularly preferred polyoxyalkylenepolyamines include polyethyleneoxidediamine, polypropyleneoxidediamine, polypropyleneoxidetriamine, diethyleneglycolpropylenediamine, triethyleneglycolpropylenediamine, polytetramethyleneoxidediamine, polyethyleneoxide-co-polypropyleneoxidediamine, and polyethyleneoxide-co-polyproyleneoxidetriamine.

Examples of suitable commercially available polyoxyalkylenepolyamines include various JEFFAMINES from Huntsman Chemical Company such as the D, ED, and EDR series diamines (e.g., D-400, D-2000, D-5000, ED-600, ED-900, ED-2001, and EDR-148), and the T series triamines (e.g., T-403), as well as H221 from Union Carbide Company.

The polyamine may also comprise the condensation reaction product of diprimary amine-terminated material (i.e., the two terminal groups are primary amine) and one or more materials containing at least two groups reactive with primary amine (referred to herein at times as "difunctional primary amine-reactive material"). Such materials are preferably substantially linear so as to have the following general structure $E-(L-E)_u-L-E$ in which each E is the residue of the diprimary amine-terminated material and each L is a linking group that is the residue of the difunctional primary amine-reactive material. (By "residue" is meant those portions of the diprimary amine-terminated material and the difunctional primary amine-reactive material that remain after reaction to form the polyamine adduct.)

The E and L groups are independently selected. That is, each E group may be the same or may be different, as may each L group, although it is preferred that each E group be the same and that each L group be the same. Preferably E and L are selected so as to form a complex that is soluble in acrylic monomer. The majority (more than 50%) of the terminal groups in the polyamine should be primary amine.

The value of u is selected so as to provide both a polyamine and a complex of useful viscosity. Preferably both the polyamine and the complex are liquid at room temperature. ("Room temperature" refers to, herein, a temperature of about 20° to 22° C.) Consequently, the value of u may be greater than or equal to zero, although a value of about 0 to 5 is more preferred, and a value of 0 or 1 is most preferred.

The diprimary amine-terminated material may be alkyl diprimary amine, aryl diprimary amine, alkylaryl diprimary amine, a polyoxyalkylenediamine (such as those described above), or mixtures thereof. Useful alkyl diprimary amines include those having the structure $NH_2-R^{10}-NH_2$ wherein $R^{10}$ is a linear or branched alkyl group having about 1 to 12 carbon atoms such as 1,3-propane diamine, 1,6-hexanediamine, and 1,12-dodecanediamine. Other useful alkyl diprimary amines include triethylene tetraamine and diethylene triamine. Examples of useful aryl diprimary amines include 1,3- and 1,4-phenylene diamine as well as the various isomers of diaminonaphthalene. An example of a useful alkylaryl diprimary amine is m-tetramethylxylene diamine.

Difunctional primary amine-reactive materials contain at least two groups reactive with primary amine. The reactive groups may be different, but it is preferred that they be the same. Difunctional primary amine-reactive materials having a functionality of 2 (i.e., two groups reactive with primary amine) are preferred. Useful difunctional primary amine-reactive materials may be generally represented by the formula $Y-R^{11}-Z$ wherein $R^{11}$ is a divalent organic radical such as an alkyl, aryl or alkylaryl group or combination thereof, and Y and Z are groups reactive with primary amine and which may be the same or may be different. Examples of useful Y and Z groups reactive with primary amine include carboxylic acid (—COOH), carboxylic acid halide (—COX, where X is a halogen, for example chlorine), ester (—COOR), aldehyde (—COH),

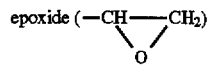

amine alcohol (—NHCH$_2$OH), and

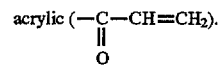

Suitable carboxylic acid-functional materials are preferably those which are useful in forming polyamides, for example, cyclohexane-1,4-dicarboxylic acid and dicarboxylic acids having the structure HOOC—$R^2$—COOH in which $R^{12}$ is a linear alkyl group having about 2 to 21 carbon atoms. Aromatic dicarboxylic acids (e.g., terephthalic and isophthalic acids) may be used as can alkylaryl dicarboxylic acids, especially in combination with alkyl dicarboxylic acids.

Useful carboxylic halide acid-functional materials and ester-functional materials include those which are obtained by derivatizing the above-described carboxylic acid-functional materials.

Suitable aldehyde-functional materials include alkyl, aryl and alkylaryl dialdehydes such as oxaldehyde propanedialdehyde, succinaldehyde, adipaldehyde, 2-hydroxyhexanedial, phthalaldehyde, 1,4,benzenediacetaldehyde, 4,4(ethylenedioxy)dibenzaldehyde, and 2,6-naphthalene dicarbaldehyde. Most preferred are glutaraldehyde and adipaldehyde.

Suitable epoxide-functional materials include aliphatic, cycloaliphatic and glycidyl ether diepoxides. Most preferred are the diepoxides based upon bis-phenol A and bis-phenol F.

Useful acrylic-functional materials are preferably diacrylates and a wide variety of such materials may be successfully employed in the invention.

The organoborane polyamine complex may be readily prepared using known techniques. Typically, the polyamine is combined with the organoborane in an inert atmosphere with slow stirring. An exotherm is often observed and cooling of the mixture is, therefore, recommended. If the ingredients have a high vapor pressure, it is desirable to keep the reaction temperature below about 70° to 80° C. Once the materials have been well mixed the complex is permitted to cool to room temperature. No special storage conditions are required although it is preferred that the complex be kept in a capped vessel in a cool, dark location.

The organoborane polyamine complex is employed in an effective amount, which is an amount large enough to permit acrylic monomer polymerization to readily occur to obtain an acrylic polymer of high enough molecular weight for the desired end use. If the amount of organoborane polyamine complex is too low, then the polymerization may be incomplete or, in the case of adhesives, the resulting composition may have poor adhesion. On the other hand, if the amount of organoborane polyamine complex is too high, then the polymerization may proceed too rapidly to allow for effective mixing and use of the resulting composition.

Large amounts of complex could also lead to the generation of large volumes of borane, which, in the case of an adhesive, could weaken the bondline. The useful rate of polymerization will depend in part on the method of applying the composition to a substrate. Thus, a faster rate of polymerization may be accomodated by using a high speed automated industrial adhesive applicator rather than by applying the composition with a hand applicator or by manually mixing the composition.

Within these parameters, an effective amount of the organoborane polyamine complex is an amount that preferably provides about 0.03 to 1.5 weight % boron, more preferrably about 0.08 to 0.5 weight % boron, most preferably about 0.1 to 0.3 weight % boron. The weight % of boron in a composition is based on the total weight of the acrylic group-containing materials plus organic thickener, (e.g., poly(methyl methacrylate) or core-shell polymer), if present, and does not include the polyol or polyisocyanate. It may be calculated by the following equation:

$$\frac{\text{(weight of complex in the composition)} \times \text{(weight \% of boron in the complex)}}{\text{(Total weight of acrylic group-containing materials + organic thickener)}}$$

Quite advantageously, the organoborane polyamine complex is carried by (e.g., dissolved in or diluted by) polyol or blend of polyols reactive with isocyanate. The polyol should not be reactive toward, coordinate or complex the polyamine. Any of a wide variety of polyols that are used to make polyurethane may be used in the invention including polyether polyols and polyester polyols. Such materials are described in various publications such as: *Polyurethane Elastomers*, published by Elsevier Applied Science, London, 1992; *Advances in Polyurethane Technology*, chapter 3, edited by Buist and Gudgeon, published by John Wiley and Sons, New York, 1968; and *Polyurethane Handbook*, edited by Oertel, published by Hanser Publishers, Munich, 1985.

While useful materials broadly have a hydroxyl functionality greater than 1, it is more preferred that the functionality be in the range of 2 to 3. The polyol should be soluble in acrylic monomers included in the composition. By "soluble" it is meant that no evidence of gross phase separation at room temperature is visible to the unaided eye. Similarly, the organoborane polyamine complex should be soluble in the polyol although slight warming of a mixture of the complex and the polyol may be helpful in forming a solution of the two at room temperature. Preferably the polyol is a liquid. Most preferably the organoborane polyamine complex and polyol form a liquid solution. Quite advantageously, substantial amounts (e.g., more than 75% by weight) of the complex may be dissolved in polyol, which facilitates the provision of two-part adhesives that can be combined in a commercially useful mix ratio.

Preferably, the polyol is selected so as to provide a polyurethane/polyurea component having a glass transition temperature greater than room temperature, more preferably greater than 30° C. While the hydroxyl groups in the polyol may be secondary or tertiary, polyols having primary hydroxyl groups are preferred so as to tailor the rate of the polyurethane polymerization to a more useful level.

Polyether polyols are particularly preferred for use in the invention and may comprise the polymerization product of epoxide with either water or polyhydric alcohol. Illustrative epoxides that may be employed in the preparation of polyether polyols useful in the invention include short chain (e.g., about 2 to 6 carbon atoms) alkylene oxides such as ethylene oxide, propylene oxide, butylene oxide and amylene oxide; glycidyl ethers such as t-butyl glycidyl ether and phenyl glycidyl ether; and random or block copolymers of two or more of these epoxides.

Exemplary polyhydric alcohols that may be employed in making polyether polyols suitable for use in the invention preferably have from two to eight hydroxyl groups and include short chain diols (e.g., having about 2 to 7 carbon atoms) such as ethylene glycol, 1,2-propane diol, 1,4-butane diol, 1,3-butane diol, 1,5-pentane diol, and 1,7-heptane diol; compounds derived from phenols such as bis-phenol A; and materials having more than two hydroxyl groups such as gycerol, 1,1,1-trimethylolpropane, 1,1,1-trimethylolethane, hexane-1,2,6-triol, α-methyl glucoside, pentaerythritol, pentatols, hextols, and various sugars (e.g., glucose, sucrose, fructose and maltose). As a subclass, polyalkylene polyether polyols (sometimes referred to herein as polyalkylene oxide polyols) are preferred. They may be prepared from the short chain alkylene oxides described previously as well as other starting materials such as tetrahydrofuran and epihalohydrins such as epichlorohydrin. Alkylene oxide tetrahydrofuran copolymers may also be used. Also useful are arylene oxides such as styrene oxide which can be used to form polyarylene oxide polyols. The most preferred polyalkylene polyether polyols are polypropylene oxide polyol, polyethylene oxide polyol, and polytetramethylene oxide polyol, including ethylene oxide or propylene oxide-terminated derivatives thereof. Most preferred are polypropylene oxide polyols. Examples of useful, commercially available polyalkylene polyether polyols include the REZOL family of materials from Witco Chemical Co. (e.g., ET-700) and the ARCOL family of materials from ARCO Chemical Co. (e.g., PPG 425 and PPG 1000).

Polyester polyols are also useful and may be prepared by reacting one or more diols with one or more dicarboxylic acids. Diols which may be used to make polyester polyols useful in the invention include saturated diols having the general structure $HO-(CH_2)_x-OH$ where the integral value of x is about 2 to 6, examples of which include ethylene glycol, propylene glycol, 1,4-butane diol, and 1,6-hexane diol. Dicarboxylic acids which may be used to make polyester polyols useful in the invention include saturated dicarboxylic acids having the general structure $HOOC-(CH_2)_y-COOH$ where the integral value of y is about 4 to 8, examples of which include adipic acid and sebacic acid. Aromatic dicarboxylic acids may also be used so long as the organoborane polyamine complex remains soluble therein. Examples of suitable commercially available polyester polyols include the FOMREZ family of materials from Witco Chemical Co. (e.g., 1066–187).

Polyester polyols based on poly-ε-caprolactone are particularly preferred and can be obtained from a ring-opening polymerization of ε-caprolactone. The TONE family of poly-ε-caprolactone polyols from Union Carbide Corp. (e.g., TONE 0210, 0305 and 0310) are particularly useful.

As noted above, the polymerization initiator systems of the invention include a polyisocyanate (i.e., a material having an isocyanate functionality greater than 1, more preferably an isocyanate functionality of 2 to 4, most preferably an isocyanate functionality of 2.). The polyisocyanate reacts with the polyamine of the organoborane polyamine complex, thereby removing the organoborane from chemical attachment with the polyamine and forming polyurea. The organoborane is available to initiate the free-radical polymerization of acrylic monomers. Quite advantageously, however, the polyisocyanate is also reactive with the polyol which carries the organoborane polyamine complex and polymerizes to a linear polymer or network of polyurethane/polyurea. As a result, the invention provides a fully reactive, 100% solids polymerizable composition.

Desirable polyisocyanates readily form reaction products with polyamine and polyol at or below (and, more preferably, at) room temperature so as to provide a composition such as an adhesive that can be easily used and cured under ambient conditions. Polyisocyanates useful in the invention are soluble in acrylic monomers used in the adhesive composition, by which it is meant that no evidence of gross phase separation at room temperature is visible to the unaided eye.

Polyisocyanates useful in the invention include various aliphatic, cycloaliphatic, aromatic, and mixed (cyclo) aliphatic-aromatic diisocyanates. In general, aliphatic diisocyanates are preferred, especially in conjunction with organoborane polyamine complexes that incorporate aliphatic polyamines.

Among the useful diisocyanates are ethylene diisocyanate, ethylidene diisocyanate, propylene diisocyanate, butylene diisocyanate, hexamethylene diisocyanate (including dimers and trimers thereof), dichlorohexamethylene diisocyanate, cyclopentylene-1,3-diisocyanate, cyclohexylene-1,4-diisocyanate, cyclohexylene-1,2-diisocyanate, isophorone diisocyanate, furfurylidene diisocyanate, toluene diisocyanate, 2,2-diphenylpropane-4,4'diphenylmethane diisocyanate, p-phenylene diisocyanate, m-phenylene diisocyanate, xylylene diisocyanate, 1,4-naphthylene diisocyanate, 1,5-naphthylene diisocyanate, m-tetramethyl xylylene diisocyanate, polymeric versions of 4,4'-methylene diphenyl diisocyanate, diphenyl-4,4'diisocyanate, azobenzene-4,4'diisocyanate, diphenylsulphone-4,4'-diisocyanate, and 1-chlorobenzene-2,4-diisocyanate. Highly crystalline aromatic materials that are insoluble in acrylic monomer (e.g., pure 4,4'-methylene diphenyldiisocyanate) would not be used.

Various tri- and tetraisocyanates may also be used such as 4,4',4"-triisocyanatotriphenylmethane, 1,3,5-triisocyanatobenzene, 2,4,6-triisocyanatotoluene, and 4,4'dimethyldiphenylmethane-2,2',5,5'-tetraisocyanate.

Hexamethylene diisocyanate (and its dimers), isophorone diisocyanate, and m-tetramethyl xylylene diisocyanate are preferred.

The polyisocyanate is employed in an effective amount; that is, an amount effective to promote both acrylic monomer polymerization by liberating organoborane from the complex and to permit the formation of a polyurethane/polyurea of sufficient molecular weight for the intended end use (but without materially adversely affecting the properties of the ultimate polymerized composition). The amount of polyisocyanate employed is typically in the same range as conventionally used for condensation polymerization of polyurethane/polyurea.

Larger amounts of polyisocyanate may permit the acrylic monomer polymerization to proceed too quickly and, in the case of adhesives, the resulting materials may demonstrate inadequate adhesion to low energy surfaces. Undesirable side reactions that adversely affect the performance properties of the polymerized composition, or an undesirably high level of extractables in the polymerized composition may also result from using large amounts of polyisocyanate that otherwise remain unreacted. If small amounts of polyisocyanate are employed, the rate of polymerization may be too slow and the monomers that are being polymerized may not adequately increase in molecular weight. However, a reduced amount of polyisocyanate may be helpful in slowing the rate of polymerization if it is otherwise too fast.

Within these parameters, the polyisocyanate may be provided in an amount wherein the number of equivalents of isocyanate is stoichiometric with the number of equivalents of amine functionality plus the number of equivalents of hydroxyl functionality in the polymerizable composition (whether or not they are provided by the polyamine, the polyol, and the polyisocyanate or other amine-, hydroxyl- or isocyanate-functional materials in the composition).

Optionally, the adhesive composition may contain a bireactive compound in order to link the polyurethane/polyurea and acrylic. The bireactive compound preferably comprises at least one free-radically polymerizable group and at least one group reactive with amine. Examples of bireactive compounds useful in the invention can be represented by the following general structure:

(Fp)$_a$—Y—(A)$_b$ wherein "Fp" is a free-radically polymerizable group; "A" is an amine-reactive group; "Y" is a polyvalent organic linking group; "a" represents the number of free-radically polymerizable groups; and "b" represents the number of amine-reactive groups.

Free-radically polymerizable group "Fp" preferably comprises an alkene group. The alkene group may be unsubstituted or substituted or part of a cyclic ring structure. Substituted alkenes include those alkenes having alkyl or aryl group substitution. Preferred alkenes are those having terminal unsubstituted double bonds such as allyl groups. Even more preferred alkenes are styryls. The most preferred alkenes are acrylic-group containing materials. Amine-reactive group "A" preferably comprises an isocyanate group. Because the bireactive compound comprises at least one free radically polymerizable group and at least one amine-reactive group, the value of each of "a" and "b" is at least one. Preferably, the sum of "a" and "b" is less than or equal to six, more preferably less than or equal to four, most preferably two. Polyvalent organic linking group "Y" may comprise a wide variety of different chemical structures depending on the reagents used to prepare the bireactive compound.

Preferably, the bireactive compound comprises the reaction product of a polyisocyanate and a hydroxyl compound containing a free-radically polymerizable group. Polyisocyanates useful in forming the bireactive compound include those discussed above as suitable for reacting with the polyamine portion of the organoborane polyamine complex.

Adducts prepared by reacting a molar excess of polyisocyanate with an active hydrogen containing compound (e.g., polyols, polythiols, and polyamines) are also useful in preparing the the bireactive compound. Useful polyols include alkylene glycols, alkylene ether glycols and, polyhydroxy alkanes. Useful polythiols include 1,3-propanedithiol, 2,2'-dimercapto diethyl ether, 2,2'-dimercapto diethyl sulfide, triethylene glycol dimercaptan, and trimethylolethane tri(3-mercaptopropionate). Useful polyamines include ethylenediamine, 1,3-diaminopropane, 1,6-hexanediamine, and 4,7,10-trioxa-1,13-tridecanediamine.

Preferred hydroxyl compounds include hydroxylated (meth)acrylates and (meth)acrylamides, wherein the use of the parenthetical expression "(meth)" indicates that the methyl substitution is optional. Adducts of hydroxylated (meth)acrylates or (meth)acrylamides with lactones (e.g., ε-caprolactone), so as to form hydroxy(meth)acrylate polyesters, are also particularly useful.

The most preferred bireactive compounds comprise the reaction product of the preferred polyisocyanates referred to above and a hydroxylated (meth)acrylate such as hydroxyethylmethacrylate, hydroxyethylacrylate, hydroxybutylacrylate or adducts of these hydroxylated (meth)acrylates with ε-caprolactone.

The bireactive compound may be included in the adhesive composition as a preformed material or it may be generated in situ. If provided as a preformed material, the starting ingredients (for example, hydroxylated (meth)acrylate and diisocyanate) are reacted in the presence of a urethane formation catalyst (such as dibutyltindilaurate) and, optionally, free radical inhibitor (e.g., hydroquinone). As an example, when the starting ingredients are a monohydroxylated (meth)acrylate and diisocyanate, the molar ratio of the former to the latter is preferably 0.9–1.1:1; more preferably 1:1, so as to provide an NCO to OH equivalent ratio of 2:1.

Alternatively, the bireactive compound may be formed in situ by including, for example, the hydroxylated (meth)acrylate, with the polyisocyanate and acrylic monomer (as explained more fully below), in the presence of a urethane formation catalyst. In this instance, the total amount of polyisocyanate should be increased to account for the additional hydroxyl functionality contributed by the hydroxylated (meth)acrylate. Thus, the compositions of the invention may also include a compound such as a hydroxylated (meth)acrylate or the others described above, which react with polyisocyanate to yield a bireactive compound.

As noted above, the liberated organoborane initiates the free-radical polymerization of acrylic monomer. By "acrylic monomer" is meant polymerizable monomers having one or more acrylic or substituted acrylic moieties, chemical groups or functionality; that is, groups having the general structure

wherein R is hydrogen or an organic radical and R' is an organic radical. Where R and R' are organic radicals, they may be the same or they may be different. Blends of acrylic monomers may also be used. The polymerizable acrylic monomer may be monofunctional, polyfunctional or a combination thereof.

The most useful monomers are monofunctional acrylate and methacrylate esters and substituted derivatives thereof such as hydroxy, amide, cyano, chloro, and silane derivatives as well as blends of substituted and unsubstituted monofunctional acrylate and methacrylate esters. Particularly preferred monomers include lower molecular weight methacrylate esters such as methyl methacrylate, ethyl methacrylate, methoxy ethyl methacrylate, hydroxyethyl methacrylate, hydroxypropyl methacrylate, cyclohexyl methacrylate, tetrahydrofurfuryl methacrylate, and blends thereof.

Both acrylate esters and higher molecular weight methacrylate esters are less preferred for use alone, but can be especially usefully employed as modifying monomers with predominating amounts of lower molecular weight methacrylate esters so as to, for example, enhance the softness or flexibility of the ultimate adhesive composition. Examples of such acrylate esters and higher molecular weight methacrylate esters include methyl acrylate, ethyl acrylate, isobornyl methacrylate, hydroxypropyl acrylate, butyl acrylate, n-octyl acrylate, 2-ethylhexyl acrylate, 2-ethylhexyl methacrylate, decylmethacrylate, dodecyl methacrylate, tert-butyl methacrylate, acrylamide, N-methyl acrylamide, diacetone acrylamide, N-tert-butyl acrylamide, N-tert-octyl acrylamide, N-butoxyacrylamide, gamma-methacryloxypropyl trimethoxysilane, 2-cyanoethyl acrylate, 3-cyanopropyl acrylate, tetrahydrofurfuryl chloroacrylate, glycidyl acrylate, glycidyl methacrylate, and the like.

Particularly preferred are blends of any of the lower molecular weight alkyl methacrylate esters described above with alkyl acrylates having 4 to 10 carbon atoms in the alkyl group, such as blends of methyl methacrylate and butylacrylate. Polymerizable compositions of this type may broadly comprise, based on the total weight of the composition, about 2 to 40 wt. % of the alkyl acrylate and, correspondingly, about 60 to 98 wt. % of the alkyl methacrylate.

Another class of polymerizable monomers that are especially useful as modifiers, such as for improving the creep resistance or temperature resistance of the ultimate composition, corresponds to the general formula:

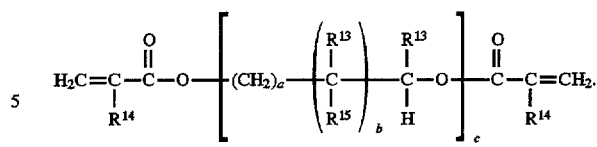

$R^{13}$ may be selected from the group consisting of hydrogen methyl, ethyl, and

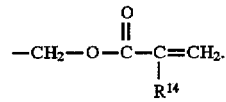

$R^{14}$ may be selected from the group consisting of chlorine, methyl and ethyl. $R^{15}$ may be selected from the group consisting of hydrogen, and

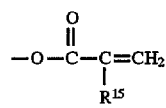

The value of a is an integer greater than or equal to 1, more preferably, from 1 to about 8, and most preferably from 1 to 4. The integral value of b is greater than or equal to 1, more preferably, from 1 to about 20. The value of c is 0 or 1.

Other acrylic monomers useful as modifying monomers, include ethylene glycol dimethacrylate, ethylene glycol diacrylate, polyethylene glycol diacrylate, tetraethylene glycol dimethacrylate, diglycerol diacrylate, diethylene glycol dimethacrylate, pentaerythritol triacrylate, trimethylolpropane trimethacrylate, as well as other polyether diacrylates and dimethacrylates.

Other polymerizable monomers that are useful in the invention, particularly as modifying monomers, have the general formula:

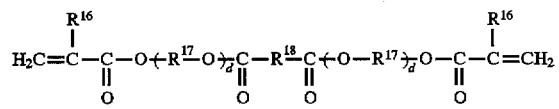

$R^{16}$ may be hydrogen, chlorine, methyl or ethyl; $R^{17}$ may be an alkylene group with 2 to 6 carbon atoms; and $R^{18}$ is $(CH_2)_e$ in which e is an integer of 0 to 8, or one of the following:

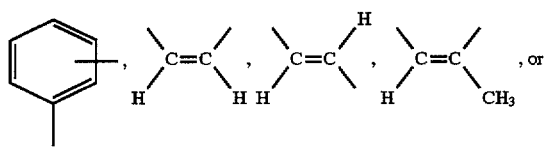

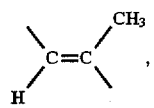

the phenyl group being substitutable at any one of the ortho, meta or para positions. The value of d is an integer of 1 to 4.

Typical monomers of this class include dimethacrylate of bis(ethylene glycol)adipate, dimethacrylate of bis(ethylene glycol)maleate, dimethacrylate of bis(ethylene glycol) phthalate, dimethacrylate of bis(tetraethylene glycol)

phthalate, dimethacrylate of bis(tetraethylene glycol) sebacate, dimethacrylates of bis(tetraethylene glycol) maleate, and the diacrylates and chloroacrylates corresponding to the dimethacrylates, and the like.

Also useful as modifying agents are monomers that are isocyanate-hydroxyacrylate or isocyanate-aminoacrylate reaction products. These may be characterized as acrylate terminated polyurethanes and polyureides or polyureas. Such monomers have the following general formula:

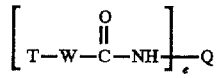

where W is selected from the group consisting of —O— and

$R^{19}$ is selected from the group consisting of hydrogen and lower alkyl groups (e.g., 1 to 7 carbon atoms). T is the organic residue of an active hydrogen-containing acrylic ester, the active hydrogen having been removed and the ester being hydroxy or amino substituted on the alkyl portion thereof (including the methyl, ethyl and chlorine homologs). The integral value of e is from 1 to 6. Q is a mono- or polyvalent organic radical selected from the group consisting of alkyl, alkylene, alkenyl, cycloalkyl, cycloalkylene, aryl, aralkyl, alkaryl, poly(oxyalkylene), poly (carboalkoxyalkylene), and heterocyclic radicals, both substituted and unsubstituted.

Typical monomers of this class include the reaction product of mono- or polyisocyanates, for example, toluene diisocyanate, with an acrylate ester containing a hydroxy or an amino group in the non-acrylate portion thereof, for example, hydroxyethyl methacrylate.

The compositions may further comprise a variety of optional additives. One particularly useful additive is a thickener such as medium (about 100,000) molecular weight polymethyl methacrylate which may be incorporated in an amount of about 10 to 40 weight %, based on the total weight of the composition. Thickeners may be employed to increase the viscosity of the composition to a more easily room temperature applied viscous syrup-like consistency.

Another particularly useful additive is an elastomeric material. These materials can improve the fracture toughness of compositions made therewith which can be beneficial when, for example, bonding stiff, high yield strength materials such as metal substrates that do not mechanically absorb energy as easily as other materials, such as flexible polymeric substrates. Such additives can be incorporated in an amount of about 5% to 35% by weight, based on the total weight of the composition.

Certain graft copolymer resins such as particles that comprise rubber or rubber-like cores or networks that are surrounded by relatively hard shells, these materials often being referred to as "core-shell" polymers, are particularly useful elastomeric additives. Most preferred are the acrylonitrile-butadiene-styrene graft copolymers. In addition to improving the fracture toughness of the composition, core-shell polymers can also impart enhanced spreading and flow properties to the uncured composition. These enhanced properties may be manifested by a reduced tendency for the composition to leave an undesirable "string" upon dispensing from a syringe-type applicator, or sag or slump after having been applied to a vertical surface. Use of more than about 20% of a core-shell polymer additive is desirable for achieving improved sag-slump resistance.

Another useful adjuvant is an acrylic monomer crosslinking agent. Acrylic monomer crosslinking agents can be used to enhance the solvent resistance of the adhesive bond, although certain compositions of the invention have good solvent resistance even in the absence of externally added acrylic monomer crosslinking agents. Typically employed in an amount of about 0.2 to 10 weight % based on the total weight of the composition, useful acrylic monomer crosslinkers include the various diacrylates referred to above as possible acrylic modifying monomers as well as other materials. Particular examples of suitable acrylic monomer crosslinking agents include ethylene glycol dimethacrylate, ethylene glycol diacrylate, triethyleneglycol dimethacrylate, diethylene glycol bismethacryloxy carbonate, polyethylene glycol diacrylate, tetraethylene glycol dimethacrylate, diglycerol diacrylate, diethylene glycol dimethacrylate, pentaerythritol triacrylate, trimethylolpropane trimethacrylate, as well as other polyether diacrylates and dimethacrylates.

Peroxides may be optionally included (typically in an amount of about 2% by weight or less, based on the total weight of the acrylate and methacrylate components) for example, to adjust the speed at which the compositions polymerize or to complete the acrylic monomer polymerization.

Catalysts that promote the formation of polyurethane (e.g., dibutyl tin dilaurate, stannous octoate, and triethylenetriamine such as DABCO from Air Products and Chemicals Co., etc.) may also be employed. A catalytically effective amount is used, which is an amount sufficient to increase the rate of polyurethane polymerization but without accelerating the polymerization such that the adhesive composition cures so quickly that it becomes difficult to spread under normal room temperature application conditions. A typical amount of polyurethane formation catalyst is less than about 2.0% by weight of the polyol.

Other additives which may be included in the compositions are those which are associated with polyurethane formation such as low molecular weight chain extenders (e.g., 1,4-butane diol, 1,3-propane diamine, etc.) which could be included to influence the nature of the polyurethane/polyurea, especially the hard segment component thereof. The hard segment of the polyurethane can also be modified by appropriate selection of the polyamine component of the complex. Thus, the polyamine can serve the dual function of stabilizing the organoborane against oxidation and providing a polyurethane hard segment.

Small amounts of inhibitors such as hydroquinone may be used, for example, to prevent or reduce degradation of the acrylic monomers during storage. Inhibitors may be added in an amount that does not materially reduce the rate of polymerization or the ultimate properties of an adhesive or other composition made therewith, typically about 100–10, 000 ppm based on the weight of the polymerizable monomers. Other possible additives include non-reactive colorants, fillers (e.g., carbon black), etc.

The various optional additives are employed in an amount that does not significantly adversely affect the polymerization process or the desired properties of compositions made therewith.

Polymerizable adhesive compositions according to the invention may be used in a wide variety of ways, including as sealants, coatings, and injection molding resins. They may also be used as matrix resins in conjunction with glass and metal fiber mats such as in resin transfer molding operations. They may further be used as encapsulants and potting compounds such as in the manufacture of electrical components, printed circuit boards and the like. Quite desirably, they provide polymerizable adhesive compositions that can bond a diverse myriad of substrates, including polymers, wood, ceramics, concrete, and primed metals.

Polymerizable compositions of the invention are especially useful for adhesively bonding low surface energy plastic or polymeric substrates that historically have been very difficult to bond without using complicated surface preparation techniques, priming, etc. By low surface energy substrates is meant materials that have a surface energy of less than 45 mJ/m$^2$, more typically less than 40 mJ/m$^2$ or less than 35 mJ/m$^2$. Included among such materials are polyethylene, polypropylene, acrylonitrile-butadiene-styrene, and fluorinated polymers such as polytetrafluoroethylene (TEFLON) which has a surface energy of less than 20 mJ/m$^2$. (The expression "surface energy" is often used synonymously with "critical wetting tension" by others.) Other polymers of somewhat higher surface energy that may be usefully bonded with the compositions of the invention include polycarbonate, polymethylmethacrylate, and polyvinylchloride.

The polymerizable compositions of the invention can be easily used as two-part adhesives. The acrylic monomers are blended as would normally be done when working with such materials, although they should be thoroughly dried to preclude undesirable reaction between the polyisocyanate and moisture that could cause foaming and carbon dioxide evolution. The polyisocyanate is usually included in this blend so as to separate it from the organoborane polyamine complex, thus providing one part of the two-part composition. The optional bireactive compound (if present) is also added to the first part of the adhesive composition. The organoborane polyamine complex, polyol, and any polyurethane formation catalyst provide the second part of the composition. The first and second parts are combined shortly before it is desired to use the composition.

For a two-part adhesive such as those of the invention to be most easily used in commercial and industrial environments, the ratio at which the two parts are combined should be a convenient whole number. This facilitates application of the adhesive with conventional, commercially available dispensers. Such dispensers are shown in U.S. Pat. Nos. 4,538,920 and 5,082,147 and are available from Conprotec, Inc. (Salem, N.H.) under the tradename "Mixpac."

Typically, these dispensers use a pair of tubular receptacles arranged side-by-side with each tube being intended to receive one of the two parts of the adhesive. Two plungers, one for each tube, are simultaneously advanced (e.g., manually or by a hand-actuated ratcheting mechanism) to evacuate the contents of the tubes into a common, hollow, elongated mixing chamber that may also contain a static mixer to facilitate blending of the two parts. The blended adhesive is extruded from the mixing chamber onto a substrate. Once the tubes have been emptied, they can be replaced with fresh tubes and the application process continued.

The ratio at which the two parts of the adhesive are combined is controlled by the diameter of the tubes. (Each plunger is sized to be received within a tube of fixed diameter, and the plungers are advanced into the tubes at the same speed.) A single dispenser is often intended for use with a variety of different two-part adhesives and the plungers are sized to deliver the two parts of the adhesive at a convenient mix ratio. Some common mix ratios are 1:1, 1:2, 1:4 and 1:10.

If the two parts of the adhesive are combined in an odd mix ratio (e.g. 3.5:100), then the ultimate user would probably manually weigh the two parts of the adhesive. Thus, for best commercial and industrial utility and for ease of use with currently available dispensing equipment, the two parts of the adhesive should be capable of being combined in a common, whole number mix ratio such as 10:1 or less, more preferably 1:4, 1:3, 1:2 or 1:1.

Adhesive compositions of the invention are uniquely suited for use with conventional, commercially available dispensing equipment for two-part adhesives. The unique solubility of the organoborane polyamine complex in polyol can be advantageously used to modify the mix ratio of the two parts of the adhesive composition to the most commercially important whole number values; e.g., 1:10, 1:4, 1:3, 1:2 or 1:1. In addition, the excellent solubility of the organoborane polyamine complex in polyol permits the complex to be stored apart from the acrylic monomer-containing part of the two-part composition. As a result, the two parts of the composition have excellent storage stability (at least several weeks) but can still be combined in a commercially useful mix ratio. Moreover, the polyisocyanate reacts with the polyol and the polyamine to form a linear polymer or network of polyurethane/polyurea independent from the linear polymer or network of acrylic.

Once the two parts have been combined, the composition should be used quickly, as the useful pot life may be short depending upon the acrylic monomer mix, the amount of complex, the temperature at which the bonding is to be performed, the presence or absence of a polyurethane formation catalyst, and the type of hydroxyl groups in the polyol.

The polymerizable composition can be easily applied and cured at room temperature. Typically, it is applied to one or both substrates and then the substrates are joined together with pressure to force excess composition out of the bond line. This also has the advantage of displacing composition that has been exposed to air and that may have begun to oxidize. In general, the bonds should be made shortly after the composition has been applied, preferably within about 10 minutes. The typical bond line thickness is about 0.1 to 0.3 mm. The bonding process can easily be carried out at room temperature and to improve the degree of polymerization it is desirable to keep the temperature below about 40° C., preferably below 30° C., and most preferably below about 25° C.

Once applied, the composition develops cohesive strength from the simultaneous polymerization of acrylic monomer (to form a linear polymer or network of acrylic) and the polyisocyanate, polyol and polyamine (to form a linear polymer or network of polyurethane/polyurea independent from but coexisting with the linear polymer or network of acrylic). Adhesion is provided by the acrylic component. The bonds will cure to a reasonable green strength to permit handling of the bonded components within about 6 to 7 hours. Full strength will be reached in about 24 hours under ambient conditions; post-curing with heat (typically about 80° C.) may be used if desired. Even more rapid strength build-up is facilitated by the inclusion of a bireactive compound in the polymerizing mixture to crosslink the acrylic and polyurethane/polyurea with each other, and the use of aromatic polyisocyanate. In such situations, handling strength can be reached in less than 1 hour.

The acrylic monomer, polyamine portion of the complex, polyol and polyisocyanate should be selected so as to yield a cured adhesive in which the independent polyurethane/polyurea and acrylic components are compatible. By "compatible" it is meant that no evidence of gross phase separation of the acrylic and polyurethane/polyurea is visible to the unaided eye at room temperature such that the resulting adhesive bonds are characterized by low cohesive strength and inconsistent adhesion.

The invention will be more fully appreciated with reference to the following nonlimiting examples in which the weights are given as either weight percents (weight %), based on the total weight of the composition which is nominally 100 weight %, or grams, the weights (except for boron) being reported to two significant digits following the decimal point.

Various tradenames and abbreviations used in the examples are defined according to the following schedule:

| Abbreviation or Tradename | Description |
|---|---|
| BA | n-butyl acrylate |
| BLENDEX B467 | Acrylonitrile-butadiene-styrene terpolymer from General Electric Specialty Chemicals, Parkersburg, WV |
| cm | Centimeter |
| DBTDL | Dibutylindilaurate |
| DESMOPHEN 1150 | Castor oil based polyether-polyester polyol from Bayer. |
| DYTEK A | 2-methyl-1,5-diaminopentane, available from E. I. duPont deNemours and Co. |
| FOMREZ 1066-187 | Polyester polyol reaction product of trimethylol propane and 1,6-hexanedioic acid, available from Witco Chemical Co. |
| FOMREZ UL-28 | Polyurethane formation catalyst, available from Witco Chemical Co. |
| HA | n-hexylacrylate |
| HEMA | Hydroxyethylmethacrylate |
| HMDA | 1,6-hexanediamine |
| in. | Inch |
| IPDI | Isophorone diisocyanate |
| Lo-PMMA | low molecular weight poly (methyl methacrylate) from Aldrich Chemical Company |
| μm | Micron |
| mm | Millimeter |
| MMA | Methylmethacrylate |
| PMMA | 101,000 molecular weight poly (methyl methacrylate-co-ethyl acrylate) with less than 5% ethylacrylate from Aldrich Chemical Company |
| PPG 425 | Polypropylene oxide polyol having an approximate number average molecular weight of about 425, available from Aldrich Chemical Company |
| PPG 1000 | Polypropylene oxide polyol having an approximate number average molecular weight of about 1000, available from Aldrich Chemical Company |
| REZOL ET-700 | Polyoxyalkylene polyol commercially available from Witco Chemical Co. |
| TEB | Triethylborane |
| THFMA | Tetrahydrofurfurylmethacrylate |
| TMXDI | Tetramethylxylenediisocyanate |
| TONE 0210 | Poly-ε-caprolactane diol, available from Union Carbide Corp. |
| TONE 0305 | Poly-ε-caprolactane triol, available from Union Carbide Corp. |
| TONE 0310 | Poly-ε-caprolactone triol, available from Union Carbide Corp. |

Synthesis of Organoborane Polyamine Complex

All glassware was washed and fired at 1000° F. or was fired by means of a Bunsen burner until the glassware glowed orange. A glove box was set up and flushed with nitrogen. The oxygen concentration in the glove box was monitored by a Servomex Oxygen analyzer and the syntheses were carried out in a nitrogen environment that contained less than 100 ppm oxygen.

The glove box contained a pressure equalizing dropping funnel, an electrical balance, a flask with appropriate stoppers, a stand, and an ice bath. The organoborane was weighed into the pressure equalizing dropping funnel and the polyamine was weighed into the flask. The organoborane was then added dropwise to the polyamine with stirring and cooling. A mild exotherm was observed and the addition of organoborane was moderated to control the exotherm. If fuming occurred, the organoborane addition was slowed until the fuming subsided.

When all of the organoborane had been added, the flask was allowed to equilibrate to room temperature and either a crystalline mass or a liquid resulted. If a crystalline mass resulted, it was heated to 55° C. by means of an oil bath outside of the glove box until a liquid was obtained. The liquid was then transferred to a vial that had been flushed with nitrogen. Unless noted otherwise, the complexes were synthesized neat with a primary nitrogen atom to boron atom ratio of 1:1.

Preparation of Monomer Mixtures

More specific details about the monomer mixtures used in the examples are given below in conjunction with the individual examples. In general, however, the monomer mixtures were generated by weighing methyl methacrylate, n-butyl acrylate, thickener (e.g., poly(methyl methacrylate) or core shell polymer), and bireactive compound (if included) into a bottle. The monomers were first dried over 4 Å molecular sieves. The bottle was sealed, placed on a roller/mixer, and heated under an infrared heat lamp that rendered the bottle warm but not hot to the touch until a solution was obtained. After cooling, polyisocyanate was added. Usually a clear, colorless moderately viscous liquid resulted. In the Tables, monomer ratios are given as a weight % of the monomer mixture.

Preparation of Curative Mixtures

More specific details about the curative mixtures used in the examples are given below in conjunction with the individual examples. In general, however, curative mixtures were made by dissolving the organoborane polyamine complex in polyol, using gentle heat as necessary to dissolve the complex. Polyurethane formation catalyst (if included) was also added. The polyols were first heated under vacuum to over 100° C. to remove water and then stored over 4 Å molecular sieves.

Lap Shear Strength Test Method

Examples that were subsequently evaluated to measure the lap shear strength of adhesive bonds made therewith were tested as described below. Dimensions in English units are nominal and conversion to metric units is approximate.

More specifically, the test specimens used were similar to that described in ASTM D-1002 except that they were generated using finger panels of nominal dimensions 1 in.×4 in.×⅛ in. thick (2.5 cm×10.2 cm×0.3 cm thick). 0.5 in. (1.3 cm) wide red lithographers tape was applied to the end of one of the adherends in order to fixture the bond and also to aid in making the overlap region be 0.5 in. (1.3 cm). Short pieces of piano wire measuring 0.006 in. (150 μm) diameter for examples 1 and 2 and 0.008 in. (200 μm) diameter for all other examples were used as spacers to control the thickness of the adhesive bondline.

The adhesive composition was made by weighing previously prepared monomer mixture into a vial that was capable of being sealed with a poly cap. Previously prepared curative mixture was then added, blended with the monomer mixture using a wooden stick, and the vial was sealed with the poly cap. In general, the addition of the curative mixture to the monomer mixture caused the blend to slightly exotherm and, in some cases, turn yellow.

A dab of the mixed adhesive was applied to each adherend and spread to make sure that a 1 in.×0.5 in. (2.5 cm×1.3 cm) area was covered at the end of each adherend. Two pieces of piano wire were placed into the adhesive on one adherend and the bond was closed and fixtured with the lithographers tape. The bond was further fixtured with two binder clips and allowed to cure at room temperature for 48 hours at which time the binder clips and tape were removed.

Lap shear testing was done with three types of adherends: mechanical grade TEFLON, high density polyethylene, and polypropylene, as available from Precision Punch and Plastic Co. (Minneapolis, Minn.). Three adhesive bonds were made with each adherend and each adhesive combination. For each adhesive, the TEFLON was bonded first, then the high density polyethylene, and then the polypropylene.

After curing, the bonds were tested to failure using a Tensile Testing Machine. The crosshead speed was 0.1 in./minute (2.5 mm/min.) and the tests were carried out at room temperature. The lap shear strengths are an average of the three measurements and are reported in psi (pounds per square inch) to the nearest whole number.

Bonds were visually inspected after being loaded to failure to determine the failure mode. Failure of the adherends is the most preferred although cohesive failure of the adhesive composition evidences a useful formulation. Failure modes are reported in the examples based on a series of coded abbreviations which may be interpreted as follows:

| Abbreviation | Failure Mode |
| --- | --- |
| a | Good filet adhesion |
| b | One or more bonds stretched to yield of the adherend without failure |

EXAMPLE 1

Two adhesive compositions according to the invention were prepared using the formulations shown below in Table 1. In Table 1, as in many of the other tables, information pertaining to the adhesive composition is provided in condensed form with the ingredients identified by the abbreviations shown in the previous schedule and with the relative amounts of each ingredient given parenthetically. Thus, the first entry in Table 1 describes an adhesive composition in which the monomer mixture comprised 34.80 wt. % methyl methacrylate (MMA), 25.20 wt. % n-butyl acrylate (BA), 10.00 wt. % m-tetramethyl xylene diisocyanate (TMXDI), and 30.00 wt. % poly (methyl methacrylate) (PMMA). The curative mixture comprised 17.50 wt. % triethylborane* 1,6-hexane diamine (TEB* HMDA) complex, and 82.50 wt. % DESMOPHEN 1150 polyol.

The adhesive compositions were then tested for lap shear strength and failure mode using the procedure described above and with the results shown below in Table 1. The cohesive failure mode for most of the bonds indicates that adhesion was promoted by the organoborane-initiated acrylic polymer. The compositions of example 1 are useful in applications where a softer material is desired, for example, a sealant. A commercially useful 10:1 mix ratio was obtained. The lap shear strength could be increased by providing a larger amount of polyurethane/polyurea.

TABLE 1

| Adhesive Composition | | | Testing | | | | | |
| --- | --- | --- | --- | --- | --- | --- | --- | --- |
| | | Ratio of | TEFLON | | Polyethylene | | Polypropylene | |
| Monomer Mixture (Ratio) | Curative Mixture (Ratio) | Monomer Mixture to Curative Mixture | Lap Shear Strength (psi) | Failure Mode | Lap Shear Strength (psi) | Failure Mode | Lap Shear Strength (psi) | Failure Mode |
| MMA/BA/ TMXDI/PMMA (34.80/25.20/ 0.00/30.00) | TEB*HMDA/ DESMOPHEN 1150 (17.50/82.50) | 10:1 | 98 | a, c | 102 | e | 184 | e |
| MMA/BA/ TMXDI/PMMA (34.80/25.20/ 10.00/30.00) | TEB*HMDA/ PPG1000/PPG425 (17.50/37.00/ 45.50) | 10:1 | 98 | f | 246 | a, e | 124 | a, e |

-continued

| Abbreviation | Failure Mode |
| --- | --- |
| c | Mixed mode failure |
| d | Failure of the adherend |
| e | Cohesive failure within the adhesive |
| f | Adhesion failure of the adhesive |
| g | Incomplete wetting; puddling of the adhesive |

EXAMPLE 2

A series of adhesive compositions according to the invention was prepared following the procedure described above and having the formulations shown below in Table 2. The last entry in Table 2 is a comparative example which contained neither acrylic monomer nor organoborane polyamine complex. The ratios are given in wt. %. The lap shear strength of the adhesive compositions was tested and the failure mode analyzed as described above and with the results shown in Table 2.

TABLE 2

| Adhesive Composition | | | Testing | | | | | |
| --- | --- | --- | --- | --- | --- | --- | --- | --- |
| | | Ratio of | TEFLON | | Polyethylene | | Polypropylene | |
| Monomer Mixture (Ratio) | Curative Mixture (Ratio) | Monomer Mixture to Curative Mixture | Lap Shear Strength (psi) | Failure Mode | Lap Shear Strength (psi) | Failure Mode | Lap Shear Strength (psi) | Failure Mode |
| MMA/BA/ TMXDI/PMMA (36.50/26.30/ 7.20/30.00) | TEB*HMDA/ TONE 305/ FOMREZ UL-28 | 10:1 | 296 | a, e | 646 | a, e | 374 | a, d, e |

TABLE 2-continued

| Adhesive Composition | | | Testing | | | | | |
|---|---|---|---|---|---|---|---|---|
| | | | TEFLON | | Polyethylene | | Polypropylene | |
| Monomer Mixture (Ratio) | Curative Mixture (Ratio) | Ratio of Monomer Mixture to Curative Mixture | Lap Shear Strength (psi) | Failure Mode | Lap Shear Strength (psi) | Failure Mode | Lap Shear Strength (psi) | Failure Mode |
| MMA/TMXDI/ PMMA (62.80/7.20/ 30.00) | TEB*HMDA/ TONE 0305/ FOMREZ UL-28 (34.30/63.80/ 2.00) | 10:0.6 | 164 | a, f | 740 | a, b, e | 678 | a, d, e |
| MMA/TMXDI/ LoPMMA (64.90/5.10/ 30.00) | TEB*DYTEK A/ TONE 0305/ FOMREZ UL-28 (34.30/63.80/ 2.00) | 10:1 | 256 | a, f | 570 | a, e | 490 | a, d |
| MMA/BA/ TMXDI/ LoPMMA (36.70/26.20/ 7.20/30.00) | TEB*DYTEK A/TONE 0305/ FOMREZ UL-28 (31.80/66.30/ 2.00) | 10:1 | 312 | a, e | 622 | a, e | 318 | a, d, e |
| MMA/BA/ TMXDI/ PMMA (30.60/22.00/ 17.40/30.00) | TEB*HMDA/ TONE 0305/ FOMREZ UL-28 (31.80/66.30/ 2.00) | 4:1 | 318 | a, c, d | 642 | e | 470 | d, e |
| MMA/BA/ TMXDI/ PMMA (20.80/14.90/ 34.20/30.00) | TEB*HMDA/ TONE 0305/ FOMREZ UL-28 (16.10/82.00/ 2.00) | 2:1 | 250 | c | 784 | b, e | 566 | e |
| TMXDI (100.00) | TONE 0305/ FOMREZ UL-28 (99.00/1.00) | 5:7.35 | 13 | f | 146 | f | 0 | f |

In general, the failure mode was cohesive in the adhesive or the adherend stretched or failed. However, when the acrylic monomers and the organoborane polyamine complex were removed to provide the comparative example, the lap shear strength fell off significantly and the failure mode became adhesive for all substrates. Table 2 shows the use of trifunctional polyol and polyurethane formation catalysts. Table 2 also shows that commercially useful mix ratios of 10:1, 4:1 and 2:1 can be achieved with the adhesive compositions of the invention, indicating that they can be readily dispensed with commercially available dispensers for two-part adhesives.

EXAMPLE 3

A series of adhesive compositions according to the invention was prepared following the procedure described above and having the formulations shown below in Table 3. The monomer mixture included hydroxyethylmethacrylate bireactive compound to crosslink the polymerized acrylate to the polyurethane/polyurea. The component ratios (which are given in wt. %) were adjusted such that the stoichiometry of isocyanate groups to the combined amount of hydroxyl and amine groups was equal to 1:1 for each adhesive composition. The lap shear strength of the adhesive compositions was tested and the failure mode analyzed as described above and with the results shown in Table 3.

TABLE 3

| Adhesive Composition | | Ratio of Monomer Mixture to Curative Mixture | Testing | | | | | |
|---|---|---|---|---|---|---|---|---|
| | | | TEFLON | | Polyethylene | | Polypropylene | |
| Monomer Mixture (Ratio) | Curative Mixture (Ratio) | | Lap Shear Strength (psi) | Failure Mode | Lap Shear Strength (psi) | Failure Mode | Lap Shear Strength (psi) | Failure Mode |
| MMA/BA/HEMA /IPDI/PMMA /DBTDL (41.90/30.20/0.72/ 7.14/20.00/0.006) | TEB*DYTEK A/TONE 0305/DBTDL (37.40/62.50/ 0.06) | 10:1 | 252 | c | 670 | b | 976 | b, d |
| MMA/BA/HEMA /IPDI/PMMA/ DBTDL (39.10/28.10/3.36/ 9.45/20.00/0.03) | TEB*DYTEK A/TONE 0305/DBTDL (37.40/62.50/ 0.06) | 10:1 | 278 | c | 318 | b, e | 1014 | b, d |
| MMA/BA/HEMA/ IPDI/PMMA/ DBTDL (36.00/25.90/ 6.20/11.80/20.00/ 0.07) | TEB*DYTEK A/TONE 0305/DBTDL (37.40/62.50/ 0.06) | 10:1 | 230 | a, f | 206 | a, e | 308 | c, d |

Table 3 shows the improved adhesion that can be obtained when the adhesive composition includes a bireactive compound. Preferably, the bireactive compound is employed in an amount of about 0.5 to 50% based on the ratio of hydroxyl equivalents to polyisocyanate equivalents. Table 3 also shows that isophorone diisocyanate can be used as the polyisocyanate and that dibutyltindilaurate can be used as the polyurethane formation catalyst.

EXAMPLE 4

Example 4 shows an adhesive composition according to the invention in which BLENDEX B467 core shell polymer was used as a thickener rather than poly(methyl methacrylate). The monomer mixture was MMA/BA/ TMXDI/BLENDEX B467 in which the relative weight percentages of the different ingredient was: 52.00/11.30/ 6.80/30.00. The monomer mixture was prepared by mixing the different ingredients in a blender under high shear conditions until an off-white opalescent thixotropic mass was obtained. The curative mixture (prepared as described in the curative mixture preparation) was TEB*HMDA/TONE 0305/FOMREZ UL-28 in which the relative weight percentages of the different ingredients was: 32.40/67.60/0.0010. The monomer mixture and curative mixture were combined in a 10:1 ratio and lap shear strength test specimens were prepared and tested as described above and with the results shown below in Table 4.

TABLE 4

| TEFLON | | Polyethylene | | Polypropylene | |
|---|---|---|---|---|---|
| Lap Shear Strength (psi) | Failure Mode | Lap Shear Strength (psi) | Failure Mode | Lap Shear Strength (psi) | Failure Mode |
| 340 | a,b,e | 508 | a,e | 692 | e |

EXAMPLE 5

A series of adhesive compositions according to the invention was prepared in which the monomer mixtures described in Table 5 below were paired with corresponding curative mixtures shown below in Table 6. The monomer mixtures and curative mixtures were prepared as described above, although no heat was used. In Tables 5 and 6, the relative amounts of the different ingredients are given in grams (g). The lap shear strength of the adhesive compositions was tested and the failure mode analyzed as described above and with the results shown below in Table 7.

TABLE 5

| Monomer Mixture | MMA (g) | BA (g) | HEMA (g) | IPDI (g) | PMMA (g) |
|---|---|---|---|---|---|
| M1 | 5.77 | 4.15 | 1.50 | 2.57 | 6.00 |
| M2 | 5.70 | 4.10 | 1.58 | 2.65 | 6.00 |
| M3 | 5.50 | 3.94 | 1.69 | 2.89 | 6.00 |

The HEMA included 0.07% by weight DBTDL.

TABLE 6

| Curative Mixture | TEB*DYTEK A Complex (g) | N:B Ratio | TONE 0305 (g) |
|---|---|---|---|
| C1 | 1.26 | 1:1 | 3.74 |
| C2 | 0.75 | 2:1 | 4.25 |
| C3 | 1.83 | 2:1 | 3.17 |

The Tone 0305 included 0.047% by weight DBTDL. N:B refers to the ratio of primary amine nitrogen atoms to boron atoms in the complex.

As shown below in Table 7 a series of adhesive compositions was prepared in which a monomer mixture was combined with its corresponding curative in a 10:1 weight ratio. When weighed and mixed by hand, the adhesive compositions cured too quickly to be used. The adhesive compositions were then used in conjunction with a 10:1 tubular syringe type two-part adhesive dispenser that was outfitted with a static mixer.

Lap shear strength test specimens were prepared as described above but with several exceptions. Because the adhesive compositions cured rapidly, a stripe of adhesive was placed at the end of one adherend and at the end of the other adherend and the bonds were mated and compressed by hand until the wire spacers resisted further compression.

The bonds were made in the following order: TEFLON, polyethylene, polypropylene; TEFLON, polyethylene, polypropylene; TEFLON, polyethylene, polypropylene. After all nine bonds were made, they were fixtured with binder clips and allowed to cure at room temperature for 48 hours before lap shear strength testing and bond failure analysis. The test results are shown below in Table 7.

TABLE 7

| Adhesive Composition | | Testing | | | | | |
|---|---|---|---|---|---|---|---|
| | | TEFLON | | Polyethylene | | Polypropylene | |
| | | Lap Shear | | Lap Shear | | Lap Shear | |
| Monomer Mixture | Curative Mixture | Strength (psi) | Failure Mode | Strength (psi) | Failure Mode | Strength (psi) | Failure Mode |
| M1 | C1 | 199 | f | 656 | b | 118 | a, c, f |
| M2 | C2 | 79 | a, f | 667 | b | 313 | a, c, f |
| M3 | C3 | 120 | a, f | 586 | a, b, c | 375 | c, f |

Table 7 shows that the adhesive compositions of the invention can be used in conjunction with a tubular dual syringe type dispenser for two-part adhesives while providing adhesion to various low surface energy polymer surfaces. Example 5 further shows how the adhesive compositions of the invention can rapidly build strength. They cured quickly to a high lap shear strength.

EXAMPLE 6

A series of adhesive compositions according to the invention was prepared in which the monomer mixtures described in Table 8 below were paired with corresponding curative mixtures as shown below in Table 9. The monomer mixtures and curative mixtures were prepared as described above. In Tables 8 and 9, the relative amounts of the different ingredients are given in grams.

TABLE 8

| Monomer Mixture | MMA (g) | BA (g) | THFMA (g) | HA (g) | TMXDI (g) | IPDI (g) | PMMA (g) |
|---|---|---|---|---|---|---|---|
| M1 | 10.70 | 7.67 | | | 4.16 | | 7.50 |
| M2 | 10.90 | 7.83 | | | | 3.78 | 7.50 |

TABLE 8-continued

| Monomer Mixture | MMA (g) | BA (g) | THFMA (g) | HA (g) | TMXDI (g) | IPDI (g) | PMMA (g) |
|---|---|---|---|---|---|---|---|
| M3 | 11.10 | 8.00 | | | 3.39 | | 7.50 |
| M4 | 11.30 | 8.13 | | | | 3.08 | 7.50 |
| M5 | 11.30 | 8.16 | | | 3.01 | | 7.50 |
| M6 | 11.50 | 8.27 | | | | 2.73 | 7.50 |
| M7 | 8.00 | 7.24 | 2.06 | | 5.20 | | 7.50 |
| M8 | 10.06 | 5.00 | | 2.24 | 5.20 | | 7.50 |
| M9 | 10.06 | 7.24 | | | 5.20 | | 7.50 |
| M10 | 10.34 | 7.44 | | | | 4.72 | 7.50 |

TABLE 9

| Curative Mixture | TONE 030 (g) | REZOL ET-700 (g) | FOMREZ 1066-187 (g) | TONE 0210 (g) | TONE 0310 (g) | TEB*DYTEK A COMPLEX (g) |
|---|---|---|---|---|---|---|
| C1 | | 6.65 | | | | 0.85 |
| C2 | | 6.64 | | | | 0.86 |
| C3 | | | 6.63 | | | 0.87 |
| C4 | | | 6.62 | | | 0.88 |
| C5 | | | | 3.31 | 3.31 | 0.89 |
| C6 | | | | 3.31 | 3.31 | 0.89 |
| C7 | 6.69 | | | | | 0.82 |
| C8 | 6.69 | | | | | 0.82 |
| C9 | 6.69 | | | | | 0.81 |
| C10 | 6.67 | | | | | 0.83 |

In curative mixtures C1 to C8, the polyol included 1% by weight DBTDL. In curative mixtures C9 to C10, the polyol included 1% by weight Fomrez UL-28. Each complex had a 1:1 ratio of primary amine nitrogen atoms to boron atoms.

As shown below in Table 10 a series of adhesive compositions was prepared in which a monomer mixture was combined with its corresponding curative mixture at a 4:1 weight ratio. The lap shear strength of the adhesive compositions was tested and the failure mode analyzed as described above and with the results shown in Table 10.

TABLE 10

| Adhesive Composition | | TEFLON Lap Shear | | Polyethylene Lap Shear | | Polypropylene Lap Shear | |
|---|---|---|---|---|---|---|---|
| Monomer Mixture | Curative Mixture | Strength (psi) | Failure Mode | Strength (psi) | Failure Mode | Strength (psi) | Failure Mode |
| M1 | C1 | 70 | c | 76 | e | 96 | e |
| M2 | C2 | 178 | c | 206 | e | 506 | a, d, e |
| M3 | C3 | 198 | c | 530 | e | 890 | b, d |
| M4 | C4 | 208 | a, c | 594 | a, e | 1052 | b, d |
| M5 | C5 | 174 | c | 358 | a, e | 358 | a, e |
| M6 | C6 | 198 | c | 524 | e | 968 | b, d |
| M7 | C7 | 234 | c | 518 | b, e | 972 | b, d |
| M8 | C8 | 212 | c | 362 | a, e | 922 | b, d |
| M9 | C9 | 190 | c | 634 | a, b, e | 866 | a, b, d, e |
| M10 | C10 | 182 | c, f | 424 | a, e | 900 | b, d |

Table 10 shows that different polyols, acrylic monomers, polyisocyanates and polyurethane formation catalysts can be used in the adhesive compositions of the invention. Curative mixtures C5 and C6 show a blend of liquid and solid polyols, which formed a solution. The flexibility of the adhesive can be tailored by appropriate selection of the polyol and acrylic monomer. The combination of monomer mixture M1 and curative mixture C1 had adhesion but was flexible and elastomeric. Other combinations also adhered but with higher lap shear strength.

EXAMPLE 7

A series of adhesive compositions according to the invention was prepared in which the monomer mixtures described in Table 11 below were paired with corresponding curative mixtures shown below in Table 12. The monomer mixtures and curative mixtures were prepared as described above. In Tables 11 and 12, the relative amounts of the different ingredients are given in grams.

The amount of organoborane polyamine complex was varied in the adhesive compositions. In order to maintain a 1:1 stoichiometry (i.e., ratio of isocyanate groups to the combined number of hydroxyl and amine groups), the level of polyol and polyisocyanate was varied. The polyol included 0.05% by weight DBTDL. The ratio of primary amine nitrogen atoms to boron atoms in the complex was 1:1.

TABLE 11

| Monomer Mixture | MMA (g) | BA (g) | TMXDI (g) | PMMA (g) |
|---|---|---|---|---|
| M1 | 12.80 | 9.20 | 2.10 | 6.00 |
| M2 | 12.80 | 9.20 | 2.10 | 6.00 |

TABLE 11-continued

| Monomer Mixture | MMA (g) | BA (g) | TMXDI (g) | PMMA (g) |
|---|---|---|---|---|
| M3 | 12.80 | 9.20 | 2.10 | 6.00 |
| M4 | 12.70 | 9.20 | 2.10 | 6.00 |
| M5 | 12.70 | 9.20 | 2.10 | 6.00 |
| M6 | 12.70 | 9.10 | 2.20 | 6.00 |
| M7 | 12.70 | 9.10 | 2.20 | 6.00 |
| M8 | 12.60 | 9.10 | 2.30 | 6.00 |

TABLE 12

| Curative Mixture | TONE (g) | TEB*DYTEK A COMPLEX (g) |
|---|---|---|
| C1 | 5.92 | 0.080 |
| C2 | 5.76 | 0.24 |
| C3 | 5.34 | 0.66 |
| C4 | 5.18 | 0.82 |
| C5 | 4.34 | 1.66 |
| C6 | 3.48 | 2.52 |
| C7 | 2.58 | 3.42 |
| C8 | 1.38 | 4.62 |

As shown below in Table 13 a series of adhesive compositions was prepared in which a monomer mixture was combined with its corresponding curative mixture in a 10:1 weight ratio to show how varying the boron content in the adhesive composition affects lap shear strength. The lap shear strength of the adhesive compositions was tested and the failure mode analyzed as described above and with the results shown in Table 13.

TABLE 13

| Adhesive Composition | | | Testing | | | | | |
|---|---|---|---|---|---|---|---|---|
| | | | TEFLON Lap Shear | | Polyethylene Lap Shear | | Polypropylene Lap Shear | |
| Monomer Mixture | Curative Mixture | Wt. % Boron | Strength (psi) | Failure Mode | Strength (psi) | Failure Mode | Strength (psi) | Failure Mode |
| M1 | C1 | 0.01 | 2 | f | 3 | f | 13 | f |
| M2 | C2 | 0.03 | 1 | f | 327 | c | 30 | c |
| M3 | C3 | 0.09 | 132 | c | 378 | a, e | 484 | a, e |
| M4 | C4 | 0.1 | 110 | c | 488 | e | 668 | d |
| M5 | C5 | 0.2 | 96 | c | 290 | e | 466 | a, e |
| M6 | C6 | 0.3 | 122 | c | 464 | e | 486 | d, e |
| M7 | C7 | 0.4 | 114 | a, c | 282 | e | 386 | e |
| M8 | C8 | 0.5 | 128 | c | 208 | e | 424 | e |

Table 13 shows that at boron levels (calculated as a weight percentage of the acrylate-group containing portion of the adhesive composition plus thickener, i.e., acrylic monomers and poly(methyl methacrylate)) below about 0.03 wt. %, adhesion is reduced. At about 0.03 wt. % boron the adhesion to polyethylene increases. Above about 0.08 wt. % boron, adhesion to all substrates improves. Curative mixture C8 also shows a solution comprising more than 75% by weight organoborane polyamine complex.

EXAMPLE 8

A series of adhesive compositions according to the invention was prepared in which the monomer mixtures described in Table 14 below were paired with corresponding curative mixtures shown below in Table 15. The monomer mixtures and curative mixtures were prepared as described above. In Tables 14 and 15, the relative amounts of the different ingredients are given in grams.

The amount of organoborane polyamine complex was varied in the adhesive compositions. In order to maintain a 1:1 stoichiometry (i.e., ratio of isocyanate groups to the combined number of hydroxyl and amine groups), the level of polyol and polyisocyanate was varied. The polyol included 1% by weight DBTDL. The ratio of primary amine nitrogen atoms to boron atoms in the complex was 1:1.

TABLE 14

| Monomer Mixture | MMA (g) | BA (g) | TMXDI (g) | PMMA (g) |
|---|---|---|---|---|
| M1 | 10.10 | 7.27 | 5.12 | 7.50 |
| M2 | 10.10 | 7.27 | 5.13 | 7.50 |
| M3 | 10.10 | 7.26 | 5.15 | 7.50 |
| M4 | 10.10 | 7.26 | 5.16 | 7.50 |
| M5 | 10.10 | 7.24 | 5.19 | 7.50 |
| M6 | 10.00 | 7.22 | 3.23 | 7.50 |
| M7 | 10.00 | 7.21 | 5.27 | 7.50 |
| M8 | 10.00 | 7.19 | 5.32 | 7.50 |

TABLE 15

| Curative Mixture | TONE 0305 (g) | TEB*DYTEK A COMPLEX (g) |
|---|---|---|
| C1 | 7.46 | 0.040 |
| C2 | 7.39 | 0.11 |
| C3 | 7.21 | 0.29 |
| C4 | 7.13 | 0.37 |
| C5 | 6.76 | 0.74 |
| C6 | 6.38 | 1.12 |
| C7 | 5.98 | 1.52 |
| C8 | 5.58 | 1.92 |

As shown below in Table 16 a series of adhesive compositions was prepared in which a monomer mixture was combined with its corresponding curative mixture in a 4:1 weight ratio to show how varying the boron content in the adhesive composition affects lap shear strength. The lap shear strength of the adhesive compositions was tested and the failure mode analyzed as described above and with the results shown in Table 16. The adhesive compositions nominally comprised more than 40% polyurethane/polyurea.

TABLE 16

| Adhesive Composition | | | Testing | | | | | |
|---|---|---|---|---|---|---|---|---|
| | | | TEFLON Lap Shear | | Polyethylene Lap Shear | | Polypropylene Lap Shear | |
| Monomer Mixture | Curative Mixture | Wt. % Boron | Strength (psi) | Failure Mode | Strength (psi) | Failure Mode | Strength (psi) | Failure Mode |
| M1 | C1 | 0.01 | 1 | f | 12 | f | 11 | f |
| M2 | C2 | 0.03 | 48 | f | 120 | c | 16 | e |
| M3 | C3 | 0.08 | 270 | c | 678 | a, b, e | 842 | b, d |

TABLE 16-continued

|  | Adhesive Composition | | Testing | | | | | |
|---|---|---|---|---|---|---|---|---|
| | | | TEFLON | | Polyethylene | | Polypropylene | |
| | | | Lap Shear | | Lap Shear | | Lap Shear | |
| Monomer Mixture | Curative Mixture | Wt. % Boron | Strength (psi) | Failure Mode | Strength (psi) | Failure Mode | Strength (psi) | Failure Mode |
| M4 | C4 | 0.1 | 264 | a, c, e | 664 | a, b, e | 1024 | b |
| M5 | C5 | 0.2 | 196 | a, c, e | 548 | a, e | 650 | d |
| M6 | C6 | 0.3 | 190 | cf | 378 | a, e | 378 | a, e |
| M7 | C7 | 0.4 | 152 | c, e | 262 | e | 280 | e |
| M8 | C8 | 0.5 | 106 | c, f | 154 | e | 312 | e |

Table 16 shows that at boron levels (calculated as a weight percentage of the acrylate-group containing portion of the adhesive composition plus thickener) below about 0.03 wt. %, adhesion is reduced. At about 0.03 wt. % boron the adhesion to polyethylene increases. Above about 0.08 wt. % boron, adhesion to all substrates improves. At high levels of the complex, the lap shear strength was less but adhesion was maintained.

EXAMPLE 9

A series of adhesive compositions according to the invention was prepared in which the monomer mixtures described in Table 17 below were paired with corresponding curative mixtures shown below in Table 18. The monomer mixtures and curative mixtures were prepared as described above. In Tables 17 and 18, the relative amounts of the different ingredients are given in grams.

The amount of organoborane polyamine complex was varied in the adhesive compositions. In order to maintain a 1:1 stoichiometry (i.e., ratio of isocyanate groups to the combined number of hydroxyl and amine groups), the level of polyol and polyisocyanate was varied. The polyol included 1% by weight DBTDL. The ratio of primary amine nitrogen atoms to boron atoms in the complex was 1:1.

TABLE 17

| Monomer Mixture | MMA (g) | BA (g) | TMXDI (g) | PMMA (g) |
|---|---|---|---|---|
| M1 | 7.13 | 5.13 | 10.20 | 7.50 |
| M2 | 7.13 | 5.13 | 10.30 | 7.50 |
| M3 | 7.12 | 5.12 | 10.30 | 7.50 |
| M4 | 7.11 | 5.12 | 10.30 | 7.50 |

TABLE 17-continued

| Monomer Mixture | MMA (g) | BA (g) | TMXDI (g) | PMMA (g) |
|---|---|---|---|---|
| M5 | 7.10 | 5.11 | 10.30 | 7.50 |
| M6 | 7.08 | 5.09 | 10.30 | 7.50 |
| M7 | 7.06 | 5.08 | 10.40 | 7.50 |
| M8 | 7.04 | 5.07 | 10.40 | 7.50 |

TABLE 18

| Curative Mixture | TONE 0305 (g) | TEB*DYTEK A COMPLEX (g) |
|---|---|---|
| C1 | 14.90 | 0.029 |
| C2 | 14.90 | 0.086 |
| C3 | 14.80 | 0.23 |
| C4 | 14.70 | 0.29 |
| C5 | 14.40 | 0.59 |
| C6 | 14.10 | 0.89 |
| C7 | 13.80 | 1.20 |
| C8 | 13.50 | 1.53 |

As shown below in Table 19 a series of adhesive compositions was prepared in which a monomer mixture was combined with its corresponding curative mixture at a 2:1 weight ratio to show how varying the boron content in the adhesive composition affects lap shear strength. The lap shear strength of the adhesive compositions was tested and the failure mode analyzed as described above and with the results shown in Table 19.

TABLE 19

|  | Adhesive Composition | | Testing | | | | | |
|---|---|---|---|---|---|---|---|---|
| | | | TEFLON | | Polyethylene | | Polypropylene | |
| | | | Lap Shear | | Lap Shear | | Lap Shear | |
| Monomer Mixture | Curative Mixture | Wt. % Boron | Strength (psi) | Failure Mode | Strength (psi) | Failure Mode | Strength (psi) | Failure Mode |
| M1 | C1 | 0.01 | 0 | f | 0 | f | 0 | f |
| M2 | C2 | 0.03 | 0 | f | 21 | f | 0 | f |
| M3 | C3 | 0.08 | 146 | c, f | 698 | a, b, e | 336 | a, c |
| M4 | C4 | 0.1 | 159 | f | 634 | a, b, e | 349 | a, c |
| M5 | C5 | 0.2 | 289 | a, c | 536 | b, f | 757 | a, d |
| M6 | C6 | 0.3 | 222 | a, c | 318 | a, e, f | 688 | e |

TABLE 19-continued

| Adhesive Composition | | | Testing | | | | | |
|---|---|---|---|---|---|---|---|---|
| | | | TEFLON | | Polyethylene | | Polypropylene | |
| | | | Lap Shear | | Lap Shear | | Lap Shear | |
| Monomer Mixture | Curative Mixture | Wt. % Boron | Strength (psi) | Failure Mode | Strength (psi) | Failure Mode | Strength (psi) | Failure Mode |
| M7 | C7 | 0.4 | 239 | a, c, e | 399 | c, e, f | 612 | c, e, |
| M8 | C8 | 0.5 | 270 | c | 414 | c, e, f | 770 | d, e |

Table 19 shows that at boron levels (calculated as a weight percentage of the acrylate-group containing portion of the adhesive composition plus thickener) below about 0.03 wt. %, adhesion is reduced. At about 0.03 wt. % boron adhesion to polyethylene increases. Above about 0.08 wt. % boron, adhesion to all substrates improves.

Predominantly acrylic adhesives are often accompanied by a distinct and pungent odor which can make them unpleasant to use. Quite desirably, however, the adhesive compositions of example 9 which, exclusive of the PMMA, were approximately ⅔ polyurethane/polyurea and ⅓ polymerized acrylic, had significantly less odor yet still provided adhesion to various low surface energy polymers.

Example 9 also evidences the ability to tailor the adhesive composition by varying the relative amounts of polyurethane/polyurea and acrylic in the cured composition. The relative amounts that are desirable will be influenced by the intended application, some applications benefitting from a larger amount of acrylic, while others will benefit from a larger amount of polyurethane/polyurea. However, it is possible to provide compositions that have the advantages associated with a polyurethane adhesive (e.g., toughness, abrasion resistance) yet still adhere to low surface energy polymers, even though polyurethane adhesives are typically associated with bonding high surface energy substrates. In such compositions, the polyurethane/polyurea will comprise more than 50% of the adhesive. More generally, however, the cured compositions of the invention may comprise from about 1 to 80% polyurethane/polyurea and, correspondingly, from about 20 to 99% acrylic, these percentages also being derivable from the relative amounts of acrylic monomer and the combined amount of polyisocyanate, polyol and polyamine in the polymerizable composition.

EXAMPLE 10

Example 10 describes the performance of a conventional two-part acrylic adhesive that was modified to also include monomers that would polymerize to polyurethane.

Part A:
14.70 g. TONE 0305 (with 0.05% by weight DBTDL)
28.60 g. HYPALON 30 (chlorosulphonated polyethylene from E. I. dupont de Nemours and Company)
53.74 g. methyl methacrylate
0.85 g. cumene hydroperoxide
Part A was generated by dissolving the various ingredients in one another.
Part B:
22.50 g. BLENDEX B467
10.00 g. TMXDI
67.50 g. methyl methacrylate
4.50 g VANAX 808 (from Vanderbilt Chemical Co.)
0.0045 g. copper napthenate Part B was generated by weighing the ingredients into a metal jar and mixing under room temperature, ambient conditions with an air-powered, high shear mixer until a brownish, translucent thixotropic fluid was obtained having minimal or no agglomerates of the BLENDEX B467 (less than 5 minutes).

The two parts of the adhesive were then weighed into a jar at a ratio of 1:1 by weight and lap shear strength test specimens were prepared as described above but with a 72 hour room temperature cure (i.e., cured over a weekend). The lap shear strength was tested and the failure mode analyzed as described above and with the results shown below in Table 20.

TABLE 20

| TEFLON | | Polyethylene | | Polypropylene | |
|---|---|---|---|---|---|
| Lap Shear Strength (psi) | Failure Mode | Lap Shear Strength (psi) | Failure Mode | Lap Shear Strength (psi) | Failure Mode |
| 5 | f | 72 | f | 34 | f |

The adhesive cured to a hard, relatively tough, yellowish-brown material that gave low lap shear strengths and failed adhesively. Example 10 shows the significant loss in performance, especially to low surface energy polymeric substrates, that occurs when the adhesive composition does not include an organoborane polyamine complex.

EXAMPLE 11

In example 11, a pair of two-part adhesives (each comprising a "Part A" and a "Part B") were formulated as follows:
Part A1:
2.50 g. PMMA
2.53 g. BA
3.53 g. MMA
1.44 g. TEB*DYTEK A organoborane polyamine complex having a 1:1 primary amine nitrogen atom to boron atom ratio.
Part B1:
10.00 g. PMMA
1.25 g. TMXDI
12.03 g. BA
16.72 g. MMA
Part A2:
2.50 g. PMMA
6.06 g. MMA
1.44 g. TEB*DYTEK A organoborane polyamine complex having a 1:1 primary amine nitrogen atom to boron atom ratio.

Part B2:
10.00 g. PMMA
1.25 g. TMXDI
14.56 g. BA
14.19 g. MMA

"Part A" of each adhesive was prepared by dissolving the acrylic monomers and PMMA in each other and then adding the organoborane polyamine complex. The initial viscosity of the solution was little changed after adding the complex. "Part B" was prepared by mixing the various components together. Each "Part B" was then combined with its corresponding "Part A" in a 4:1 weight ratio so as to provide 0.002 part boron per part by weight of the two-part adhesive composition. The lap shear strength of the two adhesive compositions was then tested immediately after combining the two parts and the failure mode of the bonds were analyzed as described above and with the results shown below in Table 21.

TABLE 21

| Adhesive Composition | | Testing | | | | | |
|---|---|---|---|---|---|---|---|
| | | TEFLON | | Polyethylene | | Polypropylene | |
| | | Lap Shear | | Lap Shear | | Lap Shear | |
| Part A | Part B | Strength (psi) | Failure Mode | Strength (psi) | Failure Mode | Strength (psi) | Failure Mode |
| A1 | B1 | 154 | c | 284 | a, e | 796 | d, e |
| A2 | B2 | 194 | c | 376 | e | 798 | d, e |

The two adhesive compositions could be used to make bonds immediately after blending "Part A" with its corresponding "Part B". Changes in the viscosity of the two parts (before mixing with each other) under ambient conditions were observed visually. After two days, the viscosity of each "Part B" had not changed appreciably. After one day, however, each "Part A" had become extremely viscous. After two days, Part A1 had become rubbery and Part A2 had become a hard solid indicating that the organoborane polyamine complex, whose presence is important for providing adhesion to low energy plastic substrates, is not storage-compatible with acrylic monomers because it causes them to become hard or rubbery in only a couple of days.

EXAMPLE 12

Two adhesive compositions according to the invention comprising, from example 8, monomer mixture 4 (M4) combined with curative mixture 4 (C4), and monomer mixture 5 (M5) combined with curative mixture 5 (C5) were stored in sealed vials under ambient conditions for about 3 weeks. There was no visible change in the adhesive compositions at the end of the storage period. The lap shear strength of the two adhesive compositions was tested at the end of the storage period using the procedure described above and with the results shown below in Table 22 along with the assessment of the failure mode. For comparison purposes, the test results for the corresponding adhesive compositions from example 8 are shown in parentheses.

TABLE 22

| Adhesive Composition | | Testing | | | | | |
|---|---|---|---|---|---|---|---|
| | | TEFLON | | Polyethylene | | Polypropylene | |
| | | Lap Shear | | Lap Shear | | Lap Shear | |
| Monomer Mixture | Curative Mixture | Strength (psi) | Failure Mode | Strength (psi) | Failure Mode | Strength (psi) | Failure Mode |
| M4 | C4 | 146 (264) | c (a, c, e) | 540 (664) | a, e (a, b, e) | 506 (1024) | d, e (b) |
| M5 | C5 | 194 (186) | c (a, c, e) | 418 (548) | a, e (a, e) | 560 (650) | d, e (d) |

Even after 3 weeks of storage, the lap shear strengths were still very good and the failure mode had not changed significantly. By contrast, the adhesive formulations of example 11 had become hard or rubbery after only two days. Thus, the two-part adhesive compositions of the invention can be combined in commercially useful mix ratios but still have excellent storage stability.

EXAMPLE 13

Two adhesive compositions were prepared to evaluate rate of strength build-up. The monomer mixtures described in Table 23 below were paired with corresponding curative mixtures shown below in Table 24. The monomer mixtures and curative mixtures were prepared as described above. In Tables 23 and 24, the relative amounts of the different ingredients are given in grams. The polyol included 1% by weight DBTDL. The ratio of primary amine nitrogen atoms to boron atoms in the complex was 1:1.

TABLE 23

| Monomer Mixture | MMA (g) | BA (g) | IPDI (g) | HEMA (g) | PMMA (g) |
|---|---|---|---|---|---|
| M1 | 11.97 | 8.61 | 1.92 | 0.00 | 7.50 |
| M2 | 11.37 | 8.18 | 2.30 | 0.50 | 7.50 |

TABLE 24

| Curative Mixture | TONE 0305 (g) | TEB*DYTEK A COMPLEX (g) |
|---|---|---|
| C1 | 2.38 | 0.62 |
| C2 | 2.39 | 0.61 |

As shown below in Table 25 adhesive compositions were prepared in which monomer mixture M1 was combined with curative mixture C1, and monomer mixture M2 was combined with curative mixture C2, each in a 10:1 weight ratio. Using each adhesive composition, 15 adhesive bonds were made with polyethylene adherends and 15 bonds were made with polypropylene adherends. At various time intervals after the bonds were made, the lap shear strength was tested following the procedure described above and with the results shown below in Table 25.

TABLE 25

| | Adhesive Composition | | | |
|---|---|---|---|---|
| | M1 + C1 | | M2 + C2 | |
| Time (hours) | Lap Shear Strength on Polyethylene (psi) | Lap Shear Strength on Polypropylene (psi) | Lap Shear Strength on Polyethylene (psi) | Lap Shear Strength on Polypropylene (psi) |
| 1 | 4 | 2 | 4 | 7 |
| 2 | 26 | 16 | 110 | 46 |
| 3 | 44 | 17 | 80 | 118 |
| 4 | 70 | 98 | 212 | 418 |
| 5 | 140 | 170 | 324 | 468 |
| 7 | 122 | 260 | 618 | 688 |
| 24 | 714 | 806 | 714 | 1006 |

The rate of strength build-up of the adhesive compositions of the invention can be advantageously and suprisingly accelerated by the presence of a bireactive compound such as hydroxyethylmethacrylate.

Various modifications and alterations of this invention will become apparent to those skilled in the art without departing from the scope and spirit of the invention. It should be understood that this invention is not limited to the illustrative embodiments set forth herein.

The embodiments for which an exclusive property or privilege is claimed are defined as follows:

1. An adhesive composition that can be applied and cured at room temperature comprising:

(a) a polymerizable blend of alkyl acrylate monomer and alkyl methacrylate monomer;

(b) an optional organic thickener;

(c) an organoborane polyamine complex which provide about 0.08 to 0.5 wt. % boron, based on the weight of the acrylic-group containing materials and optional organic thickener in the adhesive composition, the complex having the structure:

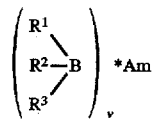

wherein:

$R^1$ is an alkyl group having 1 to 10 carbon atoms;

$R^2$ and $R^3$ are independently selected from alkyl groups having 1 to 10 carbon atoms and phenyl-containing groups;

Am is a polyamine selected from the group consisting of alkyl polyamine, polyoxyalkylenepolyamine, and the reaction product of a diprimary amine-terminated material and a material having at least two groups reactive with primary amine, wherein the number of primary amine groups in the reaction mixture was greater than the number of groups reactive with primary amine; and the value of v is selected so as to provide an effective ratio of primary amine nitrogen atoms to boron atoms in the complex;

(d) a polyol in which the organoborane polyamine complex is soluble and which is selected from the group consisting of polyethylene oxide polyol, polypropylene oxide polyol, polytetramethylene oxide polyol, ethylene oxide- and propylene oxide-terminated derivatives of these materials, poly-ε-caprolactone, and blends of the foregoing; and (e) an effective amount of a diisocyanate that reacts with the polyamine to liberate the organoborane for initiating polymerization of the polymerizable blend, and that reacts with the polyamine and the polyol to form polyurethane/polyurea.

2. A 100% solids, two-part curable adhesive composition comprising:

(a) a first part comprising a solution of organoborane polyamine complex and polyol, wherein the polyol is not reactive with the polyamine; and (b) a second part comprising:

(1) polymerizable acrylic monomer; and (2) a polyisocyanate that is soluble in the acrylic monomer, wherein the polyisocyanate is provided in an amount sufficient to react with the polyamine to liberate the organoborane for intitiating polymerization of the acrylic monomer, and to react with the polyol and the polyamine to form polyurethane/polyurea;

(3) a polyurethane formation catalyst; and (4) optionally, either a compound that has both a free-radically polymerizable group and a group reactive with amine, or a material that reacts with the polyisocyanate to form a compound that has both a free-radically polymerizable group and a group reactive with amine.

3. A 100% solids, two-part curable adhesive composition according to claim 2 wherein the polyol is selected from the group consisting of polyethylene oxide polyol, polypropylene oxide polyol, polytetramethylene oxide polyol, ethylene oxide- and propylene oxide-terminated derivatives of these materials, poly-ε-caprolactone, and blends of the foregoing.

4. A 100% solids, two-part curable adhesive composition according to claim 2 wherein the first part and the second part are combined in a whole number ratio of 1:1 to 1:10.

5. A 100% solids, two-part curable adhesive composition according to claim 2 wherein the first part and the second part are each in a different receptacle of a two-part adhesive dispenser.

6. A cured adhesive composition comprising:

(a) a polymerized acrylic;

(b) polyurethane/polyurea independent from the polymerized acrylic; and (c) organoborane and/or organoborane degradation by-product.

7. A cured adhesive composition according to claim 6 further comprising a compound that links the polymerized acrylic and the polyurethane/polyurea.

8. A cured adhesive composition according to claim 6 wherein the polyurethane/polyurea has a glass transition temperature above room temperature.

9. A bonded composite comprising a first substrate and a second substrate adhesively bonded together by a layer of a cured adhesive composition according to claim 6.

10. A bonded composite according to claim 9 wherein the first and second substrates are each independently selected from low surface energy polymeric materials.

11. A bonded composite according to claim 10 wherein the first and second substrates are each independently selected from the group consisting of polyethylene, polypropylene and polytetrafluoroethylene.

12. A method of improving the storage stability of a two-part polymerizable adhesive composition that comprises polymerizable acrylic monomer, organoborane polyamine complex, and a material that reacts with the polyamine for liberating the organoborane to initiate polymerization of the acrylic monomer, the method comprising the steps of:
(a) providing an organoborane polyamine complex;
(b) providing a polyol in which the organoborane polyamine complex is soluble;
(c) forming a solution of the polyol and the organoborane polyamine complex; and
(d) preparing a two-part polymerizable adhesive composition in which one part comprises (i) material that reacts with the polyamine and (ii) all of the polymerizable acrylic monomer, and the other part comprises the solution of the polyol and the organoborane polyamine complex.

13. In a two-part polymerizable adhesive composition that comprises polymerizable acrylic monomer, organoborane polyamine complex, and a material that reacts with the polyamine for liberating the organoborane to initiate polymerization of the acrylic monomer, a method for reducing the amount of material that can migrate in the polymerized adhesive composition, said material comprising the reaction product of the polyamine and the material that reacts with polyamine, the method comprising the steps of:
(a) providing a polyisocyanate that is reactive with the polyamine component of the complex;
(b) providing a polyol that is reactive with the polyisocyanate;
(c) permitting the polyisocyanate to react with the polyamine to liberate the organoborane;
(d) initiating polymerization of the acrylic monomer with the liberated organoborane and polymerizing the acrylic monomer to form acrylic polymer; and
(e) permitting the polyamine, polyisocyanate and polyol to react to form polyurethane/polyurea independent from but coexisting with the acrylic polymer.

14. A method according to claim 13 wherein the number of equivalents of isocyanate functionality is equal to the sum of the number of equivalents of amine functionality plus the number of equivalents of hydroxyl functionality.

15. An adhesive composition according to claim 1 wherein the number of equivalents of isocyanate functionality is equal to the sum of the number of equivalents of amine functionality plus the number of equivalents of hydroxyl functionality.

16. An adhesive composition according to claim 11 wherein the adhesive composition comprises about 0.1 to 0.3 weight % boron, based on the weight of acrylic-group containing components and optional organic thickener in the adhesive composition.

17. An adhesive composition according to claim 11 further comprising either a compound that has both a free-radically polymerizable group and a group reactive with amine, or a material that reacts with the polyisocyanate to form a compound that has both a free-radically polymerizable group and a group reactive with amine.

18. An adhesive composition according to claim 11 further comprising a hydroxylated (meth)acrylate.

19. An adhesive composition according to claim 11 further comprising a polyurethane formation catalyst.

20. A 100% solids, two-part curable adhesive composition according to claim 2 wherein the number of equivalents of isocyanate functionality is equal to the sum of the number of equivalents of amine functionality plus the number of equivalents of hydroxyl functionality.

21. A 100% solids, two-part curable adhesive composition according to claim 2 wherein the polymerizable acrylic monomer is selected from the group consisting of monofunctional acrylate ester, monofunctional methacrylate ester, substituted derivatives of the foregoing, and blends of the foregoing.

22. A 100% solids, two-part curable adhesive composition according to claim 2 wherein the adhesive composition comprises about 0.03 to 1.5 weight % boron, based on the weight of acrylic-group containing components and any organic thickener in the adhesive composition.

23. A 100% solids, two-part curable adhesive composition according to claim 22 wherein the adhesive composition comprises about 0.1 to 0.3 weight % boron, based on the weight of acrylic-group containing components and any organic thickener in the adhesive composition.

24. A 100% solids, two-part curable adhesive composition according to claim 2 wherein optional compound b(4) is present and comprises a hydroxylated (meth)acrylate.

25. A 100% solids, two-part curable adhesive composition according to claim 2 wherein the first part and the second part are combined in a whole number ratio of 1:1 to 1:4.

26. A cured adhesive composition according to claim 6 wherein the organoborane has the structure:

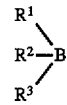

wherein:
$R^1$ is an alkyl group having 1 to 10 carbon atoms; and
$R^2$ and $R^3$ are independently selected from alkyl groups having 1 to 10 carbon atoms and phenyl-containing groups.

27. A cured adhesive composition according to claim 7 wherein the compound that links the polymerized acrylic and the polyurethane/urea had both a free-radically polymerizable group and a group reactive with amine.

28. A cured adhesive composition according to claim 27 wherein the compound that links the polymerized acrylic and the polyurethane/urea was a hydroxylated (meth)acrylate.

29. A cured adhesive composition according to claim 6 further comprising a polyurethane formation catalyst.

30. A bonded composite according to claim 9 wherein at least one of the first and second substrates is a low surface energy polymeric material.

31. A bonded composite according to claim 30 wherein the at least one substrate is formed of a material selected from the group consisting of polyethylene, polypropylene, and polytetrafluoroethylene.

32. A method according to claim 12 wherein the polyol is selected from the group consisting of polyether polyol and polyester polyol.

33. A method according to claim 32 wherein the polyol is polyalkylene oxide polyol.

34. A method according to claim 32 wherein the polyol is selected from the group consisting of polyethylene oxide polyol, polypropylene oxide polyol, polytetramethylene oxide polyol, ethylene oxide- and propylene oxide-terminated derivatives of these materials, poly-ε-caprolactone polyol, and blends of the foregoing.

35. A method according to claim 12 wherein the material that reacts with the polyamine is a polyisocyanate.

36. A method according to claim 35 wherein the polyisocyanate is soluble in the polymerizable acrylic monomer.

37. A method according to claim 35 wherein the number of equivalents of isocyanate functionality is equal to the sum of the number of equivalents of amine functionality plus the number of equivalents of hydroxyl functionality.

38. A method according to claim 22 wherein:

(a) the polyol is not reactive with the polyamine of the complex; and (b) the material that reacts with the polyamine is a diisocyanate that reacts with the polyamine to liberate the organoborane for initiating polymerization of the acrylic monomer, wherein the diisocyanate is soluble in the acrylic monomer and is reactive with both the polyamine and the polyol to form polyurethane/polyurea.

39. A method according to claim 35 wherein the polyol and the polyisocyanate are soluble in the polymerizable acrylic monomer.

40. A method according to claim 12 further comprising providing either a compound that has both a free-radically polymerizable group and a group reactive with amine, or a material that reacts with the polyisocyanate to form a compound that has both a free-radically polymerizable group and a group reactive with amine, and including the compound in said one part of the two-part composition.

41. A method according to claim 12 further comprising providing a hydroxylated (meth)acrylate in said one part of the two-part composition.

42. A method according to claim 12 further comprising providing a polyurethane formation catalyst in said other part of the two-part composition.

* * * * *

UNITED STATES PATENT AND TRADEMARK OFFICE
CERTIFICATE OF CORRECTION

PATENT NO. : 5,686,544
DATED : November 11, 1997
INVENTOR(S) : Alphonsus V. Pocius It is certified that error appears in the above-identified patent and that said Letters Patent is hereby corrected as shown below:

Column 23 and 24, Table 1,
Under Adhesive Composition/Monomer Mixture (Ratio):

"MMA/BA/ TMXDI/PMMA (34.80/25.20/ 0.00/30.00)"   should read   -- MMA/BA/ TMXDI/PMMA (34.80/25.20/ 10.00/30.00) --.

Column 34, Table 14,
Monomer Mixture/M6, under TMXDI(g), "3.23" should read -- 5.23 --.

Column 35, Table 16,
Adhesive Composition/Monomer Mixture/M5, under Testing/TEFLON/Lap Shear Strength (psi), " 196" should read -- 186 --.

Column 36, Table 19,
Adhesive Composition/Monomer Mixture/M3, under Testing/Polyethylene/Lap Shear Strength (psi), " 698" should read -- 688 --.
Adhesive Composition/Monomer Mixture/M4, under Testing/Polyethylene/Lap Shear Strength (psi), " 634" should read -- 654 --.

Column 43,
Line 51, "claim 11" should read -- claim 1 --.
Line 56, "claim 11" should read -- claim 1 --.
Line 62, "claim 11" should read -- claim 1 --.
Line 64, "claim 11" should read -- claim 1 --.

UNITED STATES PATENT AND TRADEMARK OFFICE
CERTIFICATE OF CORRECTION

PATENT NO. : 5,686,544
DATED : November 11, 1997
INVENTOR(S) : Alphonsus V. Pocius It is certified that error appears in the above-identified patent and that said Letters Patent is hereby corrected as shown below:

Column 45,
Line 7, "claim 22" should read -- claim 12 --.

Signed and Sealed this

Thirtieth Day of October, 2001

Attest:

NICHOLAS P. GODICI
Attesting Officer  Acting Director of the United States Patent and Trademark Office